(12) United States Patent
Lizos et al.

(10) Patent No.: US 8,143,253 B2
(45) Date of Patent: Mar. 27, 2012

(54) ORGANIC COMPOUNDS

(75) Inventors: Dimitrios Lizos, Basel (CH); Sven Weiler, Basel (CH); Nikolaus Johannes Stiefl, Basel (CH)

(73) Assignee: Novartis AG, Basel (CH)

( * ) Notice: Subject to any disclaimer, the term of this patent is extended or adjusted under 35 U.S.C. 154(b) by 96 days.

(21) Appl. No.: 12/670,188

(22) PCT Filed: Jul. 24, 2008

(86) PCT No.: PCT/EP2008/059705
§ 371 (c)(1),
(2), (4) Date: Jan. 22, 2010

(87) PCT Pub. No.: WO2009/013335
PCT Pub. Date: Jan. 29, 2009

(65) Prior Publication Data
US 2010/0204235 A1    Aug. 12, 2010

(30) Foreign Application Priority Data
Jul. 26, 2007   (EP) ..................... 07113214

(51) Int. Cl.
*A01N 43/58* (2006.01)
*A61K 31/50* (2006.01)
*C07D 237/26* (2006.01)
(52) U.S. Cl. .................. 514/248; 544/235; 544/236
(58) Field of Classification Search .................. 544/235, 544/236; 514/248
See application file for complete search history.

(56) References Cited

U.S. PATENT DOCUMENTS
7,750,000 B2    7/2010  Prien et al.

FOREIGN PATENT DOCUMENTS
| WO | 97/29109 A1 | 1/1997 |
| WO | 2004/076458 A1 | 9/2004 |
| WO | 2006/107784 A1 | 10/2006 |
| WO | 2007/038314 A | 4/2007 |
| WO | 2008/094556 A2 | 8/2008 |

OTHER PUBLICATIONS

Vippigunta et al.*

* cited by examiner

*Primary Examiner* — Paul V. Ward
(74) *Attorney, Agent, or Firm* — John B. Alexander

(57) ABSTRACT

Compounds of formula I

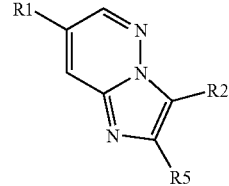

in free or salt or solvate form, where R1, R2 and R5 have the meanings as indicated in the specification, are useful for treating diseases mediated by the ALK-5 and/or ALK-4 receptor. Pharmaceutical compositions that contain the compounds and processes for preparing the compounds are also described.

7 Claims, No Drawings

ORGANIC COMPOUNDS

This application is the National Stage of Application No. PCT/EP2008/059705, filed on Jul. 24, 2008, which claims benefit under 35 U.S.C. §119(a)-(d) or (f) or 365(b) of EP Application No. 07113214.6, filed Jul. 26, 2007, the contents of which are incorporated herein by reference in their entirety.

This invention relates to organic compounds and their use as pharmaceuticals, in particular for the treatment of inflammatory or obstructive airways diseases such as pulmonary hypertension, pulmonary fibrosis, liver fibrosis; cancer; muscle diseases such as muscle atrophies and muscle dystrophies, and systemic skeletal disorders such as osteoporosis.

In one aspect, the present invention provides a compound of formula I

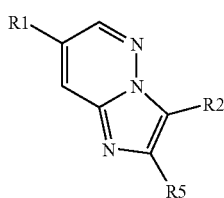

in free or salt or solvate form, wherein
R1 is aryl or heterocyclyl,
R1 being optionally substituted by one or more groups R3 independently selected from: hydroxyl, carbonyl, aminocarbonyl, $C_1$-$C_7$ alkylaminocarbonyl, amino, $C_1$-$C_7$ alkylamino, $C_1$-$C_7$ alkylthio, sulfonylamino, carbonylamino, $C_1$-$C_7$ alkylcarbonylamino, halo, carboxy, $C_1$-$C_7$ alkoxy, benzyloxy, $C_1$-$C_7$ alkyloxycarbonyl, aminosulfonyl, $C_1$-$C_7$ alkyl, cyano, sulfonyl, sulfanyl, sulfoxide, aryl, heterocyclyl, carbonyloxy, amino $C_1$-$C_7$ alkyl, $C_1$-$C_7$ alkylamino-$C_1$-$C_7$ alkyl, and further aryl-$C_1$-$C_7$alkyl, heterocyclyl-$C_1$-$C_7$-alkyl, $C_4$-$C_{15}$-cycloalkenyl and $C_2$-$C_8$-cycloalkynyl; and when R3 includes two groups, such R3 groups may be joined together to form a ring which is fused to R1;
wherein R3 is optionally substituted by one or more groups selected from hydroxyl, $C_1$-$C_7$ alkyl, aryl, amino, $C_1$-$C_7$ alkylamino, heterocyclyl, cyano, halo, sulfonyl, sulfanyl, sulfoxide, di($C_1$-$C_7$) alkylamino, hydroxyl-$C_1$-$C_7$ alkyl, alkoxy, di-$C_1$-$C_7$ alkylamino-$C_1$-$C_7$ alkyl;
R2 is aryl, heteroaryl, heteroaryl-aryl, heteroaryl-heterocyclyl, aryl-heterocyclyl, biaryl, heterocyclyl-heterocyclyl;
R2 being optionally substituted by one or more groups R4 independently selected from aryl, heteroaryl, heterocycloalkyl, $C_1$-$C_7$ alkyl, $C_3$-$C_{10}$-cycloalkyl, aminocarbonyl, $C_1$-$C_7$ alkylaminocarbonyl, halo, $C_1$-$C_7$ alkoxy, $C_1$-$C_7$ alkylthio, hydroxyl, $C_1$-$C_7$ alkylcarbonyl, carboxy, carbonyl, cyano, sulfonamide, and (further) from $C_4$-$C_{15}$-cycloalkenyl; and when R4 includes two groups, such R4 groups may be joined together to form a ring which is fused to R2;
wherein R4 is optionally substituted by one or more groups selected from hydroxyl, $C_1$-$C_7$ alkyl, aryl, amino, $C_1$-$C_7$ alkylamino, heterocyclyl, cyano, halo, sulfonyl, sulfanyl, sulfoxide;
R5 is H or $NH_2$.

Terms used in the specification have the following meanings:

"Optionally substituted" as used herein means the group referred to can be unsubstituted, or substituted at one or two or three positions by any one or any combination of the radicals listed thereafter.

"Halo" or "halogen" as used herein denotes a element belonging to group 17 (formerly group VII) of the Periodic Table of Elements, which may be, for example, fluorine, chlorine, bromine or iodine.

"$C_1$-$C_7$ alkyl" as used herein denotes straight chain, branched or cyclic alkyl that contains one to seven carbon atoms and which may be substituted by one or more radicals.

"Aryl", as used herein, represents carbocyclic aryl or biaryl. Preferably, it denotes an aromatic group having 6- to 15-ring carbon atoms. It can be monocyclic, bicyclic or tricyclic, and may be substituted by one or more radicals. Examples of $C_6$-$C_{15}$-aryl groups include but are not limited to phenyl, phenylene, benzenetriyl, indanyl, naphthyl, naphthylene, naphthalenetriyl and anthrylene.

"Heterocyclyl", refers to a 4- to 14-membered heterocyclic ring containing at least one ring heteroatom selected from the group consisting of nitrogen, oxygen and sulphur, which may be saturated, partially saturated or unsaturated. Examples of 4- to 14-membered heterocyclic groups include but are not limited to furanyl, azetidinyl, pyrrolyl, pyrrolidinyl, pyrazolyl, imidazolyl, triazolyl, isotriazolyl, tetrazolyl, thiadiazolyl, isothiazolyl, oxadiazolyl, pyridinyl, piperidinyl, pyrazinyl, oxazolyl, isoxazolyl, pyrazinyl, pyridazinyl, pyrimidinyl, piperazinyl, pyrrolidinone-yl, pyridinone-yl (e.g. 1H-pyridin-2-only), morpholinyl, triazinyl, oxazinyl, tetrahydrofuranyl, tetrahydrothiophenyl, tetrahydrothiopyranyl, tetrahydropyranyl, 1,4-dioxanyl, 1,4-oxathianyl, indazolyl, quinolinyl, indolyl, thiazolyl, thienyl, isoquinolinyl, benzothiophenyl, benzoxazolyl, benzisoxazolyl, benzothiazolyl, benzisothiazolyl, benzofuranyl, dihydrobenzofuranyl, benzodioxolyl, benzimidazolyl or tetrahydronaphthyridinyl. The 4- to 14-membered heterocyclic group can be unsubstituted or substituted.

"Heterocyclyl" includes heteroaryl and heterocycloalkyl groups.

Heteroaryl is an aromatic monocyclic or bicyclic hydrocarbon containing from 5 to 18 ring atoms one or more of which are heteroatoms selected from O, N or S. Preferably there are one or two heteroatoms. Heterocyclic aryl represents, for example: pyridyl, indolyl, quinoxalinyl, quinolinyl, isoquinolinyl, benzothienyl, benzofuranyl, benzopyranyl, benzothiopyranyl, furanyl, pyrrolyl, thiazolyl, oxazolyl, isoxazolyl, triazolyl, tetrazolyl, pyrazolyl, imidazolyl, thienyl. Heterocyclic aryl also includes such substituted radicals.

Heterocycloalkyl represents a mono-, di- or tricyclic hydrocarbon which may be saturated or unsaturated and which contains one or more, preferably one to three heteroatoms selected from O, N or S. Preferably it contains between three and 18 ring atoms. The term heterocycloalkyl is intended also to include bridged heterocycloalkyl groups such as 3-hydroxy-8-aza-bicyclo[3.2.1]oct-8-yl and fused ring systems.

"$C_3$-$C_{10}$-cycloalkyl" denotes a fully saturated carbocyclic ring having 3 to 10 ring carbon atoms, for example a monocyclic group such as a cyclopropyl, cyclobutyl, cyclopentyl or cyclohexyl, cycloheptyl, cyclooctyl, cyclononyl or cyclodecyl, or a bicyclic group such as bicycloheptyl or bicyclooctyl.

"$C_1$-$C_7$-haloalkyl" as used herein denotes $C_1$-$C_7$-alkyl as hereinbefore defined substituted by one or more halogen atoms, preferably one, two or three halogen atoms.

"$C_1$-$C_7$-alkylamino" as used herein denotes amino substituted by one or two $C_1$-$C_7$-alkyl groups as hereinbefore defined, which may be the same or different.

"$C_1$-$C_7$-alkoxy" as used herein denotes straight chain or branched alkoxy that contains 1 to 7 carbon atoms.

If R3 includes two groups, such R3 groups may be joined together to form a ring which is fused to R1, then this ring preferably has 3 to 10 ring atoms selected from carbon and up to three heteroatoms selected from N, S and O.

"$C_4$-$C_8$-cycloalkenyl" as used herein refers to a partially unsaturated carbocyclic, mono-, bi- or tri-cyclic ring with at least one double bond, such as cyclobutenyl, cyclopentenyl, e.g. cyclopenten-2- or -3-yl, cyclohexenyl, e.g. cyclohexen-2- or -3-yl, cycloheptenyl, e.g. cyclohepten-2-, -3- or -4-yl, cyclooctenyl, cyclononenyl or cyclodecenyl, or a bicyclic group such as bicycloheptenyl or bicyclooctenyl, and can be unsubstituted or substituted.

$C_2$-$C_8$-alkynyl as used herein denotes a straight or branched hydrocarbon chain that includes two to eight carbon atoms and one or more carbon-carbon triple bonds.

Where deviating numbers of carbon atoms are specified herein, such as $C_6$ or $C_4$, the definitions should be construed in accordance with the preceding definition.

Throughout this specification and in the claims that follow, unless the context requires otherwise, the word "comprise", or variations such as "comprises" or "comprising", should be understood to imply the inclusion of a stated integer or step or group of integers or steps but not the exclusion of any other integer or step or group of integers or steps. Alternatively, in another embodiment of the invention it may limit the integers and steps to those specifically mentioned, then standing for "consisting of".

According to the invention, with respect to formula (I), the following significances are preferred independently, collectively or in any combination or sub-combination:
(i) R1 is a 6-membered aryl or heteroaryl group which is optionally substituted as defined above;
(ii) R1 is phenyl or pyridinyl which is optionally substituted as defined above;
(iii) R1 is optionally substituted phenyl;
(iv) R1 is optionally substituted pyridinyl;
(v) R2 is a 6-membered aryl or heteroaryl group which is substituted at the 3-position by a heteroaryl or aryl group which is optionally substituted as defined above;
(vi) R2 is optionally substituted phenyl or pyridinyl;
(vii) R2 is optionally substituted heteroaryl-phenyl;
(viii) R2 is optionally substituted heteroaryl-pyridinyl;
(ix) R2 is optionally substituted phenyl-pyridinyl;
(x) R5 is H.

"6-membered" means having six atoms forming a ring.

Compounds of formula I that contain a basic centre are capable of forming acid addition salts, particularly pharmaceutically acceptable acid addition salts. Pharmaceutically acceptable acid addition salts of the compound of formula I include those of inorganic acids, for example, hydrohalic acids such as hydrofluoric acid, hydrochloric acid, hydrobromic acid, hydroiodic acid, nitric acid, sulfuric acid, phosphoric acid; and organic acids, for example aliphatic monocarboxylic acids such as formic acid, acetic acid, trifluoroacetic acid, propionic acid and butyric acid, caprylic acid, dichloroacetic acid, hippuric acid, aliphatic hydroxy acids such as lactic acid, citric acid, tartaric acid or malic acid, gluconic acid, mandelic acid, dicarboxylic acids such as maleic acid or succinic acid, adipic acid, aspartic acid, fumaric acid, glutamic acid, malonic acid, sebacic acid, aromatic carboxylic acids such as benzoic acid, p-chloro-benzoic acid, nicotinic acid, diphenylacetic acid or triphenylacetic acid, aromatic hydroxy acids such as o-hydroxybenzoic acid, p-hydroxybenzoic acid, 1-hydroxynaphthalene-2-carboxylic acid or 3-hydroxynaphthalene-2-carboxylic acid, and sulfonic acids such as methanesulfonic acid or benzenesulfonic acid, ethanesulfonic acid, ethane-1,2-disulfonic acid, 2-hydroxy-ethanesulfonic acid, (+) camphor-10-sulfonic acid, naphthalene-2-sulfonic acid, naphthalene-1,5-disulfonic acid or p-toluenesulfonic acid. These salts may be prepared from compounds of formula I by known salt-forming procedures. Pharmaceutically acceptable solvates are generally hydrates.

Compounds of formula I which contain acidic, e.g. carboxyl, groups, are also capable of forming salts with bases, in particular pharmaceutically acceptable bases such as those well known in the art; suitable such salts include metal salts, particularly alkali metal or alkaline earth metal salts such as sodium, potassium, magnesium or calcium salts, or salts with ammonia or pharmaceutically acceptable organic amines or heterocyclic bases such as ethanolamines, benzylamines or pyridine, arginine, benethamine, benzathine, diethanolamine, 4-(2-hydroxy-ethyl)morpholine, 1-(2-hydroxyethyl) pyrrolidine, N-methyl glutamine, piperazine, triethanolamine or tromethamine. These salts may be prepared from compounds of formula I by known salt-forming procedures. Compounds of formula I that contain acidic, e.g. carboxyl, groups may also exist as zwitterions with the quaternary ammonium centre.

Compounds of formula I in free form may be converted into salt form, and vice versa, in a conventional manner. The compounds in free or salt form can be obtained in the form of hydrates or solvates containing a solvent used for crystallisation. Compounds of formula I can be recovered from reaction mixtures and purified in a conventional manner. Isomers, such as enantiomers, may be obtained in a conventional manner, e.g. by fractional crystallisation or asymmetric synthesis from correspondingly asymmetrically substituted, e.g. optically active, starting materials.

Some compounds of the invention contain at least one asymmetric carbon atom and thus they exist in individual optically active isomeric forms or as mixtures thereof, e.g. as racemic mixtures. In cases where additional asymmetric centres exist the present invention also embraces both individual optically active isomers as well as mixtures, e.g. diastereomeric mixtures, thereof.

The invention includes all such forms, in particular the pure isomeric forms. The different isomeric forms may be separated or resolved one from the other by conventional methods, or any given isomer may be obtained by conventional synthetic methods or; by stereospecific or asymmetric syntheses. Since the compounds of the invention are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 59% of a compound of the invention.

The invention includes all pharmaceutically acceptable isotopically-labelled compounds of formula I wherein one or more atoms are replaced by atoms having the same atomic number, but an atomic mass or mass number different from the atomic mass or mass number usually found in nature. Examples of isotopes suitable for inclusion in the compounds of the invention include isotopes of hydrogen e.g. $^2H$ and $^3H$, carbon e.g. $^{11}C$, $^{13}C$ and $^{14}C$, chlorine e.g. $^{36}Cl$, fluorine e.g. $^{18}F$, iodine e.g. $^{123}I$ and $^{125}I$, nitrogen e.g. $^{13}N$ and $^{15}N$, oxygen e.g. $^{15}O$, $^{17}O$ and $^{18}O$, and sulfur e.g. $^{35}S$.

Certain isotopically-labelled compounds of formula I, for example those incorporating a radioactive isotope, are useful in drug and/or substrate tissue distribution studies. The radioactive isotopes tritium ($^3H$) and carbon-14 ($^{14}C$) are particularly useful for this purpose in view of their ease of incorporation and ready means of detection. Substitution with heavier isotopes such as deuterium (2H) may afford certain therapeutic advantages that result from greater metabolic stability, for example increased in vivo half-life or reduced dosage requirements, and hence may be preferred in some circumstances. Substitution with positron emitting isotopes, such as $^{11}C$, $^{18}F$, $^{15}O$, and $^{13}N$ can be useful in Positron Emission Topography (PET) studies for examining substrate receptor occupancy.

Isotopically-labelled compounds of formula I can generally be prepared by conventional techniques known to those skilled in the art or by processes analogous to those described in the accompanying examples using a corresponding isotopically-labelled reagent in place of the non-labelled reagent previously used.

Pharmaceutically acceptable solvates in accordance with the invention include those wherein the solvent of crystallisation may be isotopically substituted e.g. $D_2O$, $d_6$-acetone or $d_6$-DMSO.

Specific especially preferred compounds of the invention are those described hereinafter in the Examples, and/or their pharmaceutically acceptable salts.

The present invention also provides a process for the preparation of compounds of formula I in free or salt or solvate form.

According to a further aspect of the invention there is provided a process of preparing a compound of formula I comprising the step of:
(i) reacting a compound of formula X with a Suzuki coupling reagent of formula XI:

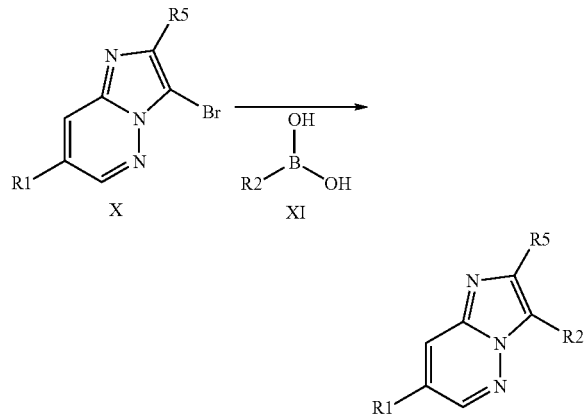

under Suzuki coupling and work-up conditions. Suitable conditions include, for example, a catalyst of $PdCl_2(PPh_3)_2$ and $Na_2CO_3$ in a suitable solvent; or
(ii) condensation of a compound of formula XII with a compound of formula XIII:

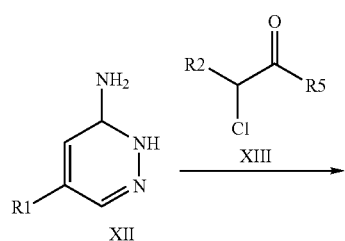

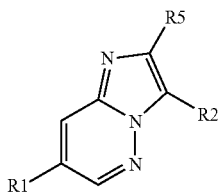

under convenient reaction conditions, e.g. $NaHCO_3$ in a suitable solvent;
wherein R1, R2 and R5 are as defined above. In each case, protecting groups may be employed and later removed following the reactions;
and, if desired, converting an obtainable free compound of the formula I into a salt, an obtainable salt of a compound of the formula I into the free form or into a different salt, and/or converting a compound of the formula I into a different compound of the formula I.

The reactions preferably take place as follows:
For reaction a, preferably the conditions of a Suzuki-Miyaura or analogue coupling reaction are employed.

The reaction given under process variant a) is preferably carried out under the conditions of a Suzuki-reaction, preferably in a mixture of a polar aprotic solvent, such as dimethylformamide (DMF), an alcohol, such as ethanol, and/or acetonitrile, and optionally water, in the presence of a catalyst for the cross-coupling, especially a noble metal catalyst, preferably a palladium catalyst, such as palladium(II) complex, for example (preferably if Hal is chloro) bis(triphenylphosphine)palladium (II) dichloride, in the presence of a base, such as potassium carbonate, sodium hydroxide or sodium carbonate, at a preferred temperature in the range from 80° C. to 160° C.; or according to a another preferred method in a cyclic ether solvent, e.g. tetrahydrofuran, and or one or more of the solvents just mentioned above, in the presence of a catalyst for the cross coupling, especially a noble metal catalyst, preferably a palladium (0) complex, for example tris (dibenzylideneacetone)-dipalladium(0) or (especially if Hal is iodo) tetrakis(triphenylphosphine)palladium(0), or of palladium dibenzylideneacetone as precursor, in the presence an appropriate ligand, such as 2-dicyclohexylphosphino-2',6'-dimethoxybiphenyl (SPhos) or 2-dicyclohexylphosphino-2'-(N,N-dimethylamino)-biphenyl (P1), and in the presence of a base, e.g. as mentioned above or potassium phosphate, and at a preferred temperatures in the range from 80 to 150° C.; if required conducting the reaction in a sealed vessel (e.g. a seal reactor) if the boiling point of the reaction mixture is exceeded and especially if (as is a preferred embodiment) the heating is effected by microwave excitation. Where required, other or additional catalyst can be added, e.g. $(PdCl_2(PPh_2)).Fe.CH_2Cl_2)$.

The reaction under b) preferably takes place in a customary solvent, such as dimethylformamide or ethanol, in the absence of presence of a base, such as sodium hydrogen carbonate, at elevated temperatures e.g. in the range from 50° C. to the reflux temperature of the reaction mixture.

Protecting Groups

If one or more other functional groups, for example carboxy, hydroxy, amino, are or need to be protected in a starting material, e.g. in any one or more starting materials, intermediates and educts, because they should not take part in the reaction or disturb the reaction, these are such groups as are usually used in the synthesis of peptide compounds, and also of cephalosporins and penicillins, as well as nucleic acid derivatives and sugars. Protecting groups are such groups that are no longer present in the final compounds once they are removed, while groups that remain as substitutents are not protecting groups in the sense used here which is groups that are added at a certain intermediate stage and removed to obtain a final compound. For example, tert-butoxy if remaining in a compound of the formula I is a substituent, while if it is removed to obtain the final compound of the formula I it is a protecting group.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by acetolysis, protonolysis, solvolysis, reduction, photolysis or also by enzyme activity, for example under conditions analogous to physiological conditions, and that they are not present in the end-products. The specialist knows, or can easily establish, which protecting groups are suitable with the reactions mentioned above and below.

The protection of such functional groups by such protecting groups, the protecting groups themselves, and their removal reactions are described for example in standard reference works, such as J. F. W. McOmie, "Protective Groups in Organic Chemistry", Plenum Press, London and New York 1973, in T. W. Greene, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (*Methods of organic chemistry*), Houben Weyl, 4th edition, Volume 15/I, Georg Thieme Verlag, Stuttgart 1974, in H.-D. Jakubke and H. Jescheit, "Aminosäuren, Peptide, Proteine" (*Amino acids, peptides, proteins*), Verlag Chemie, Weinheim, Deerfield Beach, and Basel 1982, and in Jochen Lehmann, "Chemie der Kohlenhydrate: Monosaccharide and Derivate" (*Chemistry of carbohydrates: monosaccharides and derivatives*), Georg Thieme Verlag, Stuttgart 1974.

For example, an amino protecting tert-butoxycarbonyl group can be removed by acidolysis, e.g. with trifluoroacetic acid in the presence of an appropriate solvent, such as dichloromethane, at preferred temperatures in the range from −10 to 50° C.

Optional Reactions and Conversions

A compound of the formula I may be converted into a different compounds of the formula I according to standard reaction procedures.

For example, in a compound of the formula I wherein R2 is aryl or heteroaryl, a substituent R4=halo e.g. chloro or brom, may be converted into an (unsubstituted or substituted) aryl or heteroaryl R4 by reaction with a corresponding aryl or heteroaryl compound carrying a —B(OR)$_2$ substituent wherein R is hydroxyl (or alternatively $C_1$-$C_7$-alkyl or the two R moieties together form a (unsubstituted or up to fourfold $C_1$-$C_7$-alkyl (e.g. methyl)-substituted) $C_1$-$C_4$-alkenyl bridge) under reaction conditions analogous to those mentioned above for reaction (i).

In a compound of the formula I in which R1 is substituted with R3=$C_1$-$C_7$-alkoxycarbonyl, this ester group can be converted into $C_1$-$C_7$-alkylaminocarbonyl R3 (unsubstituted or substituted as described for a compound of the formula I), e.g. in the presence of a solvent and the amine forming (after replacement of a nitrogen bound hydrogen) the unsubstituted or substituted $C_1$-$C_7$-alkylaminocarbonyl R3, where the solvent may e.g. be an alcohol, such as methanol, preferably in the presence of a base, such as a carbonate salt, e.g. sodium carbonate, and preferably at elevated temperatures, e.g. from 30 to 80° C.

In a compound of the formula I in which R1 is substituted with R3=$C_1$-$C_7$-alkoxycarbonyl, this ester group can be converted into hydroxymethyl R3 in an appropriate solvent, e.g. dichloromethane, in the presence of an appropriate complex hydride, such as diisobutylaluminium hydride, at low temperatures, e.g. in the range from 0 to −80° C.

In a compound of the formula I in which R1 is substituted with R3=$C_1$-$C_7$-alkoxycarbonyl, this ester group can be converted into free carboxyl R3 by hydrolysis with an appropriate base, e.g. an alkaline metal hydroxide, such as lithium hydroxide, in an appropriate solvent, e.g. tetrahydrofurane, water and/or an alcohol, such as methanol, at temperatures especially in the range from 0 to 50° C.

In a compound of the formula I in which R1 is substituted with carboxyl, this group can be converted into $C_1$-$C_7$-alkylaminocarbonyl (in which the alkyl is unsubstituted or substituted as described for compounds of the formula I) (that is, to the corresponding amide) by reaction in an appropriate solvent, e.g. acetonitrile or dichloromethane, in the presence of a tertiary nitrogen base, e.g. triethylamine, at preferred temperatures between 30° C. and the reflux temperature of the reaction mixture, e.g. at about 130 to 150° C. As coupling agent for amide synthesis, any reagent or reagent mixture that activates the carboxyl group in situ is possible, for example benzotriazol-1-yl-oxy-tris-(dimethylamino)-phosphonium hexafluorophosphate, with the corresponding primary (unsubstituted or substituted) $C_1$-$C_7$-alkylamine dicyclohexylcarbodiimide/1-hydroxybenzotriazole (DCC/HOBt); bis(2-oxo-3-oxazolidinyl)phosphinic chloride (BOPCl); O-(1,2-dihydro-2-oxo-1-pyridyl)-N,N,N',N'-tetramethyluronium tetrafluoroborate (TPTU); O-benzotriazol-1-yl)-N,N,N',N'-tetramethyluronium tetrafluoroborate (TBTU); (benzotriazol-1-yloxy)-tripyrrolidinophosphonium-hexafluorophosphate (PyBOP), O-(1H-6-chlorobenzotriazole-1-yl)-1,1,3,3-tetramethyluronium hexafluorophosphate, 1-(3-dimethylaminopropyl)-3-ethylcarbodiimide hydrochloride/hydroxybenzotriazole or 1-hydroxy-7-azabenzotriazole (EDC/HOBt or EDC/HOAt) or HOAt alone, or with (1-chloro-2-methyl-propenyl)-dimethylamine. For review of some other possible coupling agents, see e.g. Klauser; Bodansky, *Synthesis* (1972), 453-463.

Also in the optional process steps, carried out "if desired", functional groups of the starting compounds which should not take part in the reaction may be present in unprotected form or may be protected for example by one or more of the protecting groups mentioned hereinabove under "protecting groups". The protecting groups are then wholly or partly removed according to one of the methods described there.

Salts of a compound of formula I with a salt-forming group may be prepared in a manner known per se. Acid addition salts of compounds of formula I may thus be obtained by treatment with an acid or with a suitable anion exchange reagent. Salts with bases may be obtained with a base or with a suitable cation exchange reagent.

Salts can usually be converted to free compounds, e.g. by treating with suitable basic compounds, for example with alkali metal carbonates, alkali metal hydrogencarbonates, or alkali metal hydroxides, typically potassium carbonate or sodium hydroxide or by treating with suitable acidic compounds, e.g. hydrohalic acids, such as HCl or HBr.

Mixtures of constitutional isomers or of products and by-products can be separated according to standard procedures, e.g. by distribution, chromatography, selective crystallization or the like.

Stereoisomeric mixtures, e.g. mixtures of diastereomers, can be separated into their corresponding isomers in a manner known per se by means of suitable separation methods. Diastereomeric mixtures for example may be separated into their individual diastereomers by means of fractionated crystallization, chromatography, solvent distribution, and similar procedures. This separation may take place either at the level of a starting compound or in a compound of formula I itself. Enantiomers may be separated through the formation of diastereomeric salts, for example by salt formation with an enantiomer-pure chiral acid, or by means of chromatography, for example by HPLC, using chromatographic substrates with chiral ligands.

The invention thus also includes a compound of the formula I in isomerically pure form, or a salt and/or a solvate thereof, and its uses etc.

It should be emphasized that reactions analogous to the conversions mentioned in this chapter may also take place at the level of appropriate intermediates (and are thus useful in the preparation of corresponding starting materials).

Especially preferred (also in the case of preparation of starting materials described below) are reaction conditions and reactants as described in the examples, or analogous conditions and reactions.

The starting materials X and XII can themselves be prepared according to the following synthesis route:

TGF-β signalling requires both the ALK and type II receptors. Specifically, the type II receptor phosphorylates the GS domain of the type I receptor for TGF-β, ALK5, in the presence of TGF-β. The ALK5, in turn, phosphorylates the cytoplasmic proteins smad2 and smad3 at two carboxy terminal serines. The phosphorylated smad proteins translocate into the nucleus and activate genes that contribute to the production of extracellular matrix.

Therefore, preferred compounds of this invention are selective in that they inhibit the type I receptor.

Activins transduce signals in a manner similar to TGF-β. Activins bind to serine/thereonine kinase, the activin type II receptor (ActRIIB), and the activated type II receptor hyperphosphorylates serine/threonine residues in the GS region of the ALK4. The activated ALK4 in turn phosphorylates Smad2 and Smad3. The consequent formation of a hetero-Smad complex with Smad4 results in the activin-induced regulation of gene transcription.

Activation of the TGF-β1 axis and expansion of extracellular matrix are early and persistent contributors to the development and progression of chronic renal disease and vascular disease. Border W. A., et al, *N. Engl. J. Med.,* 1994; 331(19), 1286-92. Further, TGF-β1 plays a role in the formation of fibronectin and plasminogen activator inhibitor-1, components of sclerotic deposits, through the action of smad3 phosphorylation by the TGF-β1 receptor ALK5. Zhang Y., et al,

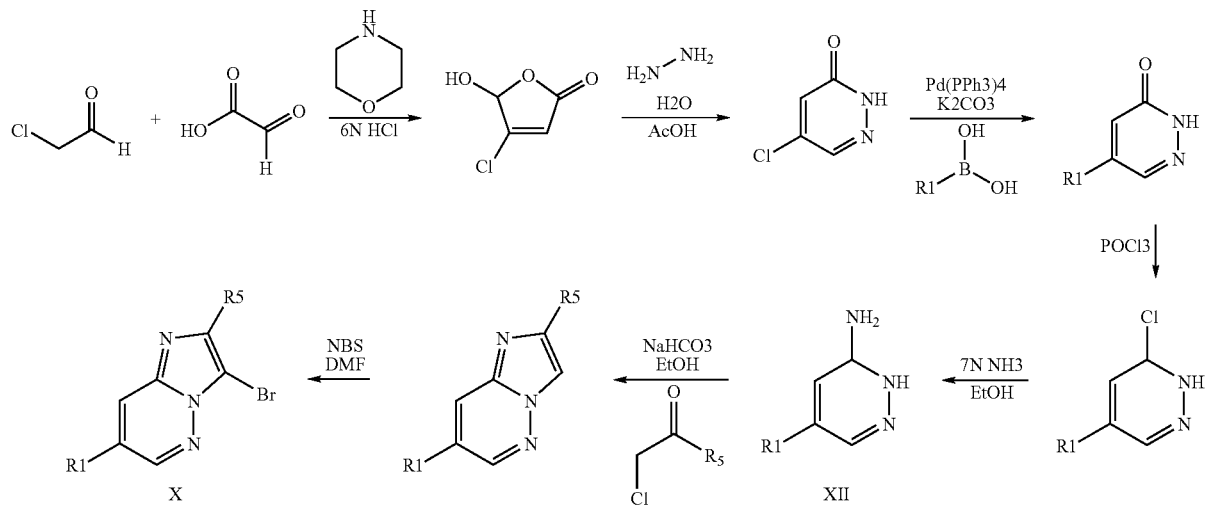

The agents of the invention act as activin-like kinase ("ALK")-5 inhibitors. At least many of these compounds also act as ALK-4 inhibitors too.

TGF-β1 is the prototypic member of a family of cytokines including the TGF-βs, activins, inhibins, bone morphogenetic proteins and Mullerian-inhibiting substance, that signal through a family of single transmembrane serine/threonine kinase receptors. These receptors can be divided into two classes, the type I or activin like kinase (ALK) receptors and type II receptors. The ALK receptors are distinguished from the type II receptors in that the ALK receptors (a) lack the serine/threonine rich intracellular tail, (b) possess serine/threonine kinase domains that are very homologous between type I receptors, and (c) share a common sequence motif called the GS domain, consisting of a region rich in glycine and serine residues. The GS domain is at the amino terminal end of the intracellular kinase domain and is critical for activation by the type II receptor. Several studies have shown that

*Nature,* 1998; 394(6696), 909-13; Usui T., et al, *Invest. Opthalmol. Vis. Sci.,* 1998; 39(11), 1981-9.

Progressive fibrosis in the kidney and cardiovascular system is a major cause of suffering and death and an important contributor to the cost of health care. TGF-β1 has been implicated in many renal fibrotic disorders. Border W. A., et al, *N. Engl. J. Med.,* 1994; 331(19), 1286-92. TGF-β1 is elevated in acute and chronic glomerulonephritis Yoshioka K., et al, *Lab. Invest.,* 1993; 68(2), 154-63, diabetic nephropathy Yamamoto, T., et al, 1993, *PNAS* 90, 1814-1818., allograft rejection, HIV nephropathy and angiotensin-induced nephropathy Border W. A., et al, *N. Engl. 5 J. Med.,* 1994; 331(19), 1286-92. In these diseases the levels of TGF-β1 expression coincide with the production of extracellular matrix. Three lines of evidence suggest a causal relationship between TGF-β1 and the production of matrix. First, normal glomeruli, mesangial cells and non-renal cells can be induced to produce extracellular-matrix protein and inhibit protease activity by exogenous TGF-β1 in vitro. Second, neutralizing anti-bodies against TGF-β1 can prevent the accumulation of extracellular matrix in nephritic rats. Third, TGF-β1 transgenic mice or in vivo transfection of the TGF-β1 gene into normal rat kidneys resulted in the rapid development of glomerulosclerosis. Kopp J. B., et al, *Lab. Invest.,* 1996; 74(6), 991 1003. Thus, inhibition of TGF-β1 activity is indicated as a therapeutic intervention in chronic renal disease.

TGF-β1 and its receptors are increased in injured blood vessels and are indicated in neointima formation following balloon angioplasty Saltis J., et al, *Clin. Exp. Pharmacol. Physiol.,* 1996; 23(3), 193-200. In addition TGF-β1 is a potent stimulator of smooth muscle cell ("SMC") migration in vitro and migration of SMC in the arterial wall is a contributing factor in the pathogenesis of atherosclerosis and restenosis. Moreover, in multivariate analysis of the endothelial cell products against total cholesterol, TGF-13 receptor ALK5 correlated with total cholesterol (P<0.001) Blann A. D., et al, *Atherosclerosis,* 1996; 120(1-2), 221-6. Furthermore, SMC derived from human atherosclerotic lesions have an increased ALK5/TGF-β type II receptor ratio. Because TGF-β1 is over-expressed in fibroproliferative vascular lesions, receptor-I variant cells would be allowed to grow in a slow, but uncontrolled fashion, while overproducing extracellular matrix components McCaffrey T. A., et al, *Jr., J. Clin.; Invest.,* 1995; 96(6), 2667-75. TGF-β1 was immunolocalized to non-foamy macrophages in atherosclerotic lesions where active matrix synthesis occurs, suggesting that non-foamy macrophages may participate in modulating matrix gene expression in atherosclerotic remodelling via a TGF-β-dependent mechanism. Therefore, inhibiting the action of TGF-β1 on ALK5 is also indicated in atherosclerosis and restenosis.

Liver fibrosis is the result of unbalanced wound healing response to chronic liver injury trigged by a number of agents, such as hepatitis B and hepatitis C virus, alcohol or drugs, and autoimmune diseases. Ultimately, liver fibrosis could lead to life-threatening cirrhosis and liver cancer (see review article by Gressner et al (2006) *J. Cell. Mol. Med.* 2006, 10(1): 76-99).

Several cellular signaling pathways are known to be altered upon chronic liver injury. TGFβ signaling, its receptors and associated Smad-signaling proteins are well documented to be present in cell types involved in fibrogenesis. The circulating levels of TGFβ have been found to be elevated in a number of animal models of fibrotic diseases including liver fibrosis. Transgenic mice with overexpression of TGFβ1 develop fibrosis in multiple organs including liver, kidney, lungs and heart. It is apparent that an elevated TGFβ signaling is involved in all types of fibrotic diseases including liver fibrosis. This notion has been further validated in several studies using TGFβ inhibitors in fibrosis models. TGFβ mediates it signal by binding to two ser/thr kinase receptors, TGFβRII and ALK5. Expressing a dominant negative TGFβRII showed beneficial effects in a rat model of dimethylnitrosamine induced liver fibrosis (see Qi et al (1999) *Proc. Natl. Acad. Sci.* 96: 2345-9 and Nakamura et al (2000) *Hepatology* 32: 247-55). Inhibiting TGFβ expression using an antisense approach also reduced liver fibrosis induced by bile duct ligation (see Arias et al (2003) BMC *Gastroenterol.* 3: 29). Recently, a small molecule inhibitor of ALK5, GW6604, when given therapeutically to rat, had significant effect in the treatment of dimethylnitrosamine induced liver fibrosis. It is quite remarkable that GW6604 prevented 40% of the death rate and inhibited extracellular matrix deposition by 60%, a key measurement for fibrosis. Importantly, no obvious side effects were noted during the 3 weeks treatment with GW6604 (see De Gouville et al (2005) *Br. J. Pharmacol.* 145: 166-77). Taken together these studies suggest that inhibiting TGFβ signaling could be an effective treatment for liver fibrotic diseases.

TGF-β1 is also indicated in wound repair. Neutralizing antibodies to TGF-β1 have been used in a number of models to illustrate that inhibition of TGF-β1 signalling is beneficial in restoring function after injury by limiting excessive scar formation during the healing process. For example, neutralizing antibodies to TGF-β1 and TGF-β2 reduced scar formation and improved the cytoarchitecture of the neodermis by reducing the number of monocytes and macrophages as well as decreasing dermal fibronectin and collagen deposition in rats Shah M., *J. Cell. Sci.,* 1995, 108, 985-1002. Moreover, TGF-β antibodies also improve healing of corneal wounds in rabbits Moller-Pedersen T., *Curr. Eye Res.,* 1998, 17, 736-747, and accelerate wound healing of gastric ulcers in the rat, Ernst H., *Gut,* 1996, 39, 172-175. These data strongly suggest that limiting the activity of TGF-β would be beneficial in many tissues and suggest that any disease with chronic elevation of TGF-β would benefit by inhibiting smad2 and smad3 signalling pathways.

TGF-β is also implicated in peritoneal adhesions Sand G. M., et al, *Wound Repair Regeneration,* 1999 November-December, 7(6), 504-510. Therefore, inhibitors of ALK5 would be beneficial in preventing peritoneal and sub-dermal fibrotic adhesions following surgical procedures.

TGF-β is also implicated in photoaging of the skin (see Fisher G J. Kang S W. Varani J. Bata-Csorgo Z. Wan Y S. Data S. Voorhees J J., Mechanisms of photoaging and chronological skin ageing, *Archives of Dermatology,* 138(11):1462-1470, 2002 November and Schwartz E. Sapadin A N. Kligman L H. "Ultraviolet B radiation increases steady state mRNA levels for cytokines and integrins in hairless mouse skin-modulation by 25 topical tretinoin", *Archives of Dermatological Research,* 290(3):137-144, 1998 March)

TGF-β signalling is also implicated in the development of pulmonary disorders, in particular pulmonary hypertension and pulmonary fibrosis (see Morrell N W, Yang X, Upton P D, Jourdan K B, Morgan N, Sheares K K, Rematch R C., Altered growth responses of pulmonary artery smooth muscle cells from patients with primary pulmonary hypertension to transforming growth factor-beta(1) and bone morphogenetic proteins. *Circulation.* 2001 Aug. 14; 104(7):790-5. Bhatt N, Baron C P, Allen J, Margo C, Marsh C B., Promising pharmacologic innovations in treating pulmonary fibrosis. *Curr Open Pharmacol.* 2006 April 28).

TGF-β1 levels are increased in animal models of pulmonary hypertension (Mata-Greenwood E, Merck B, Steinborn R H, Fireman J R, Black S M. Alterations in TGF-beta 1 expression in lambs with increased pulmonary blood flow and pulmonary hypertension. *Am. J. Physiol. Lung Cell Mol. Physiol.* 2003 July; 285(1):Lab 209-21). Other studies have suggested that pulmonary endothelial cell-derived TGF-β1 can stimulate the growth of pulmonary vascular smooth muscle cells which may underlie the enhanced muscularisation observed in the pulmonary vasculature of individuals with pulmonary hypertension (Sake S, Taraseviciene-Stewart L, Wood K, Cool C D, Norbert V F. Apoptosis of pulmonary microvascular endothelial cells stimulates vascular smooth muscle cell growth. *Am. J. Physiol. Lung Cell Mol. Physiol.* 2006 Apr. 14). Therefore, inhibiting the action of TGF-β1 on ALK5 is indicated as a therapeutic intervention in pulmonary hypertension.

Additionally, dys-regulated TGF-β signalling has also been implicated in the development of idiopathic pulmonary fibrosis. Activation of ALK5 results in Smad3-activation and downstream modulation of the expression of genes involved in the fibrotic process such as plasminogen activator inhibitor-1, pro-collagen 3A1, and connective tissue growth factor. The levels of TGF-β1 and its downstream pro-fibrotic mediators have been demonstrated to be up-regulated in bronchoalveolar lavage taken from patients with idiopathic pulmonary fibrosis (Hiwatari N, Shimura S, Yamauchi K, Nara M, Hida W, Shirato K. Significance of elevated procollagen-III-peptide and transforming growth factor-beta levels of bronchoalveolar lavage fluids from idiopathic pulmonary fibrosis patients. Tohoku J. Exp. Med. 1997 February; 181(2): 285-95) and in animal models of idiopathic pulmonary fibrosis (Westergren-Thorsson G, Hernnas J, Sarnstrand B, Oldberg A, Heinegard D, Malmstrom A. Altered expression of small proteoglycans, collagen, and transforming growth factor-beta 1 in developing bleomycin-induced pulmonary fibrosis in rats. J. Clin. Invest. 1993 August; 92(2):632-7).

Transient over-expression of active TGF-β1 in murine lungs, using adenoviral vectormediated gene transfer, resulted in progressive pulmonary fibrosis in wild-type mice, whereas no fibrosis was seen in the lungs of Smad3 knockout mice up to 28 days following TGF-β1 challenge (Khalil N, Parekh T V, O'Connor R N, Gold L I. Differential expression of transforming growth factor-beta type I and II receptors by pulmonary cells in bleomycin-induced lung injury: correlation with repair and fibrosis. Exp. Lung. Res. 2002 April-May; 28(3):233-50. Thus, inhibition of TGF-β1 activation of ALK5 is also indicated for pulmonary fibrosis.

TGF-beta 1 may also be implicated in tumors and hence the agents of the invention may be useful in the treatment of cancer, including prostate cancer, breast cancer, gastric cancer, angiogenesis, metastasis, tumors, e.g. in the treatment and/or prevention of tumor progression.

Activin signalling and overexpression of activin is linked to pathological disorders that involve extracellular matrix accumulation and fibrosis (e.g., Matsuse, T. et al., Am. J. Respir Cell Mol. Biol. 13:17-24 (1995); Inoue, S. et al., Biochem. Biophys. Res. Comm. 205:441-448 (1994); Matsuse, T. et al., Am. J. Pathol. 148:707-713 (1996); De Bleser et al., Hepatology 26:905-912 (1997); Pawlowski, J. E., et al., J. Clin. Invest. 100:639-648 (1997); Sugiyama, M. et al., Gastroenterology 114:550-558 (1998); Munz, B. et al., EMBO J. 18:5205-5215 (1999)), inflammatory responses (e.g., Rosendahl, A. et al., Am. J. Respir. Cell Mol. Biol. 25:60-68 (2001), cachexia or wasting (Matzuk7 M. M. et al., Proc. Natl. Acad. Sci. USA 91:8817-8821 (1994); Coerver, K. A. et al., Mol. Endocrinol. 10:531 543 (1996); Cipriano, S. C. et al., Endocrinology 141:2319-2327 (2000)), diseases or pathological responses in the central nervous system (e.g., Logan, A. et al., Eur. J. Neurosci. 11:2367-2374 (1999); Logan, A. et al., Exp. Neurol. 159:504-510 (1999); Masliah, E. et al., Neurochem. Int. 39:393-400 (2001); De Groot, C. J. A. et al., J. Neuropathol. Exp. Neural. 58:174-187 (1999); John, G. R. et al., Nat. Med. 8:1115-1121 (2002)) and hypertension (e.g., Dahly, A. J. et al., Am. J. Physiol. Regul. Integr Comp. Physiol. 283: R757-767 (2002)). Studies have shown that TGF-β and activin can act synergistically to induce extracellular matrix production (e.g., Sugiyama, M. et al., Gastroerterology 114; 550-558 (1998)).

It follows, therefore, that inhibition of ALK5 and/or ALK4 phosphorylation of Smad2 and Smad3 by the agents of the invention can be useful to treat and prevent disorders that involve these signalling pathways.

Activin signalling is also implicated in the development of pulmonary disorders, in particular pulmonary hypertension and pulmonary fibrosis. For example, the expression of activin A in lung samples from patients with interstitial pulmonary fibrosis demonstrated strong expression of activin A on metaplastic epithelium, hyperplastic smooth muscle cells, desquamated cells, and alveolar macrophages. Pulmonary arteries from patients with primary or secondary pulmonary hypertension showed abundant immunoreactive activin A on smooth muscle cells. These findings suggest a potential role for this growth factor, activin A, in the pathogenesis of pulmonary tissue remodelling associated with interstitial pulmonary fibrosis and pulmonary hypertension (Matsuse T, Ikegami A, Ohga E, Hosoi T, Oka T, Kida K, Fukayama M, Inoue S, Nagase T, Ouchi Y, Fukuchi Y. Expression of immunoreactive activin A protein in remodelling lesions associated with interstitial pulmonary fibrosis. Am. J. Pathol. 1996 March; 148(3):707-13). An increase in fibroblasts and associated connective tissue is a feature of pulmonary fibrosis and pulmonary hypertension. Activin A has been demonstrated to modulate human lung fibroblast (HFL1) activity, particularly with respect to proliferation and its differentiation into myofibroblast, thus activin A has potential effects on proliferation of lung fibroblast and its differentiation into myofibroblast, and may contribute to structural remodelling observed in pulmonary fibrosis and hypertension (Ohga E, Matsuse T, Teramoto S, Katayama H, Nagase T, Fukuchi Y, Ouchi Y. Effects of activin A on proliferation and differentiation of human lung fibroblasts. Biochem. Biophys. Res. Commun. 1996 Nov. 12; 228(2):391-6). The induction of pulmonary fibrosis mediated by bleomycin challenge in rats results in the up-regulated expression of activin A in macrophages infiltrated in the lung, and was detected in fibroblasts accumulated in the fibrotic area. Administration of follistatin, an antagonist of activin signalling to bleomycin-treated rats significantly reduced the number of macrophages and neutrophils in bronchoalveolar lavage and reduced the protein content. Follistatin markedly reduced the number of infiltrating cells, ameliorated the destruction of lung architecture, and attenuated lung fibrosis (Aoki F, Kurabayashi M, Hasegawa Y, Kojima I. Attenuation of bleomycin-induced pulmonary fibrosis by follistatin. Am. J. Respir. Crit. Care Med. 2005 Sep. 15; 172(6): 713-20).

Therefore, inhibiting activin signalling via ALK4 inhibition may also be beneficial for the treatment of pulmonary fibrosis and pulmonary hypertension.

It has been demonstrated recently that reduction in TGF-β signalling, through its effector Smad3, enhances the mechanical properties and mineral concentration of the bone matrix, as well as the bone mass, enabling the bone to better resist fracture. These results suggest that reduction of TGF-β signalling could be considered as a therapeutic target to treat bone disorders. (Balooch G, et al. Proc. Natl. Acad. Sci. USA. 2005 Dec. 27; 102(52):18813-8). Thus, inhibition of TGF-β1 activation of ALK5 is also indicated for increasing mineral density strength and content of bone and may be utilized to treat a wide variety of conditions, including for example, osteopenia, osteoporosis, fractures and other disorders in which low bone mineral density are a hallmark of the disease.

Having regard to their inhibition of ALK-5 and/or ALK-4 receptors, agents of the invention are useful in the treatment of conditions mediated by the ALK-5 and/or ALK-4 receptors. Treatment in accordance with the invention may be symptomatic or prophylactic.

Therefore according to a further aspect, the invention provides the use of agents of the invention in the preparation of a medicament for treating or preventing a disease or condition mediated by ALK-5 inhibition or ALK-4 inhibition.

Diseases or condition mediated by ALK-5 inhibition or ALK-4 inhibition include glomerulonephritis, diabetic nephropathy, lupus nephritis, hypertension-induced nephropathy, renal interstitial fibrosis, renal fibrosis resulting from complications of drug exposure, HIV-associated nephropathy, transplant necropathy, liver fibrosis due to all etiologies, hepatic dysfunction attributable to infections, alcohol-induced hepatitis, disorders of the biliary tree, pulmonary fibrosis, pulmonary hypertension, acute lung injury, adult respiratory distress syndrome, idiopathic pulmonary fibrosis, chronic obstructive pulmonary disease, pulmonary disease due to infectious or toxic agents, post-infarction cardiac fibrosis, congestive heart failure, dilated cardiomyopathy, myocarditis, vascular stenosis, restenosis, atherosclerosis, ocular scarring, corneal scarring, proliferative vitreoretinopathy, excessive or hypertrophic scar or keloid formation in the dermis occurring during wound healing resulting from trauma or surgical wounds, peritoneal and sub dermal adhesion, scleroderma, fibrosclerosis, progressive systemic sclerosis, dermatomyositis, polymyositis, arthritis, ulcers, impaired neurological function, male erectile dysfunction, Alzheimer's disease, Raynaud's syndrome, fibrotic cancers, tumor metastasis growth, radiation-induced fibrosis, thrombosis, and bone conditions such as osteopenia and osteoporosis, which are associated with increased calcium depletion or resorption or in which stimulation of bone formation and calcium fixation in the bone is desirable.

Diseases or conditions mediated by ALK-5 inhibition in particular include chronic renal disease, acute renal disease, wound healing, arthritis, osteoporosis, kidney disease, congetive heart failure, inflammatory or obstructive airways diseases, pulmonary hypertension, ulcers (including diabetic ulcers, chronic ulcers, gastric ulcers, and duodenal ulcers), ocular disorders, corneal wounds, diabetic nephropathy, impaired neuro-logical function, Alzheimer's disease, atherosclerosis, peritoneal and sub-dermal adhesion, any disease wherein fibrosis is a major component, including, but not limited to kidney fibrosis, lung fibrosis and liver fibrosis, for example, hepatitis B virus (HBV), hepatitis C virus (HCV), alcohol-induced hepatitis, haemochromatosis, primary biliary cirrhosis, restenosis, retroperitoneal fibrosis, mesenteric fibrosis, endometriosis, keloids, cancer, abnormal bone function, inflammatory disorders, scarring and photaging of the skin.

Inflammatory or obstructive airways diseases to which the present invention is applicable include asthma of whatever type or genesis including both intrinsic (non-allergic) asthma and extrinsic (allergic) asthma. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics. (For convenience this particular asthmatic condition is referred to as "wheezy-infant syndrome".) Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, i.e. therapy for or intended to restrict or abort symptomatic attack when it occurs, for example anti-inflammatory (e.g. corticosteroid) or bronchodilatory. Prophylactic benefit in asthma may in particular be apparent in subjects prone to "morning dipping". "Morning dipping" is a recognised asthmatic syndrome, common to a substantial percentage of asthmatics and characterised by asthma attack, e.g. between the hours of about 4 to 6 am, i.e. at a time normally substantially distant from any previously administered symptomatic asthma therapy.

Other inflammatory or obstructive airways diseases and conditions to which the present invention is applicable include adult/acute respiratory distress syndrome (ARDS), chronic obstructive pulmonary or airways disease (COPD or COAD), including chronic bronchitis, or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, e.g., acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

Preferably the disease or condition mediated by ALK-5 inhibition or ALK-4 inhibition is pulmonary hypertension, pulmonary fibrosis, liver fibrosis, muscular diseases, cancer or osteoporosis.

Pulmonary hypertension to be treated in accordance with the invention includes primary pulmonary hypertension (PPH); secondary pulmonary hypertension (SPH); familial PPH; sporadic PPH; precapillary pulmonary hypertension; pulmonary arterial hypertension (PAH); pulmonary artery hypertension; idiopathic pulmonary hypertension; thrombotic pulmonary arteriopathy (TPA); plexogenic pulmonary arteriopathy; functional classes I to IV pulmonary hypertension; and pulmonary hypertension associated with, related to, or secondary to, left ventricular dysfunction, mitral valvular disease, constrictive pericarditis, aortic stenosis, cardiomyopathy, mediastinal fibrosis, anomalous pulmonary venous drainage, pulmonary venoocclusive disease, collagen vascular disease, congenital heart disease, HIV virus infection, drugs and toxins such as fenfluramines, congenital heart disease, pulmonary venous hypertension, chronic obstructive pulmonary disease, interstitial lung disease, sleepdisordered breathing, alveolar hypoventilation disorder, chronic exposure to high altitude, neonatal lung disease, alveolar-capillary dysplasia, sickle cell disease, other coagulation disorder, chronic thromboemboli, connective tissue disease, lupus, schistosomiasis, sarcoidosis or pulmonary capillary hemangiomatosis.

Pulmonary hypertension to be treated in accordance with the invention is most particularly pulmonary hypertension associated with disorders of the respiratory system and/or hypoxemia, including chronic obstructive pulmonary disease, interstitial lung disease, sleepdisordered breathing, alveolar hypoventilation disorders, chronic exposure to high altitude, neonatal lung disease and alveolar-capillary dysplasia, but especially chronic obstructive pulmonary disease.

Lung fibrosis includes idiopathic pulmonary fibrosis in particular.

Compounds of the present may also be used to treat muscle diseases including muscular atrophies (e.g. disuse), muscular dystrophies (e.g. Duchenne's Muscle Dystrophy, Becker's Muscle Dystrophy, Limb-Girdle Muscle Dystrophy, Facioscapulohumeral Dystrophy), sarcopenia and cachexia.

Treatment of muscular diseases such as muscle atrophies and dystrophies is a largely unmet medical need. There are only few compounds approved for the use in assorted muscle disorders, mainly in the area of cancer-induced and HIV muscle wasting or cachexia, and a few more drugs are used off-label for these indications. In addition, most of these drugs only address the weight loss and do not specifically affect muscular growth and function. There is therefore a need for effective therapies to treat functional impairments associated with muscle diseases related to cachexia (e.g. in cancer, HIV and COPD), disuse atrophy, sarcopenia and dystrophy.

Myostatin, a member of the transforming growth factor β (TGFβ) family, is a key negative regulator of skeletal muscle mass. In double-muscle cattle and in a human body with skeletal muscle hypertrophy, different mutations in the myostatin gene were detected (McPherron et al (1997) *Nature* 387:83-90; Schuelke et al (2004) *N. Engl. J. Med.* 350:2682-2688). The important role of myostatin for skeletal muscle growth and disorders was confirmed in a wide variety of in vivo and in vitro studies. For example, muscle-specific overexpression of myostatin in mice causes loss of muscle mass (Reisz-Porszasz et al (2003) *AJP—Endo.* 285:876-888), whereas myostatin null mice have increased skeletal muscle mass and reduced body fat (Lin et al (2002) *Biochem. Biophys. Res. Comm.* 291: 701-706). In accordance systemic administration of myostatin induces cachexia (Zimmers et al (2002) *Science* 296:1486-1488), whereas inhibition of myostatin by, for example, the myostatin neutralizing antibody JA16 increases muscle mass and strength in wildtype and dystrophic mdx mice (Bogdanovich et al (2002) *Nature* 420: 418-421.2002; Wagner et al (2002) *Ann. Neurol.* 52: 832-836; Wolfman et al (2003) *Proc. Natl. Acad. Sci.* 100(26): 15842-15846). In addition, elevated myostatin levels have been observed in both experimental and clinical muscle atrophies such as in patients with Human Immunodeficiency Virus (HIV), cancer or liver cirrhosis as well as in sarcopenia of old age and under glucocorticoid-treatment (Ma et al (2003) *Am. J. Physiol. Endocrinol. Metab.* 285: E363-371; Gonzales-Cadavid et al (1998) *Proc. Natl. Acad. Sci.* 95: 14938-14943; see also Reisz-Porszasz et al (2003) *AJP—Endo.* 285:876-888 and Jespersen et al (2006) *Scand. J. Med. Sci. Sports.* 16: 74-82). These findings show the high potential of myostatin inhibitors as treatments for muscular atrophies and dystrophies.

The mode of action of myostatin is still under investigation. It is relatively well established that myostatin signals through Smad2/3 (Lee S. J. (2004) *Ann. Rev. Dev. Biol.* 20: 61-86). Moreover, mature myostatin has been shown to act via activin type IIb and activin receptor like kinase (ALK) receptors in adipocytes (Rebbarpragada et al (2003) *Mol. Cell. Biol.* 23: 7230-7242). However, respective findings in skeletal muscle cells are not described. Myostatin is believed to inhibit differentiation and cause atrophy via ALK signaling. Moreover, inhibition of ALK signaling promotes skMC differentiation and causes skMC hypertrophy.

Osteoporosis is a systemic skeletal disorder characterized by low bone mass and microarchitectural deterioration of bone tissue, with a consequent increase in bone fragility and susceptibility to fracture. The osteoporotic syndrome is multi faceted, encompassing primary disorders such as postmenopausal or age-related osteoporosis, and secondary conditions that accompany disease states or medications. The mechanical properties and composition of bone matrix, along with bone mass and architecture, are critical determinants of a bone's ability to resist fracture.

Thus in a further aspect the invention includes an agent of the invention for use as a pharmaceutical.

In a yet further aspect the invention includes a method for preventing or treating bone conditions which are associated with increased calcium depletion or resorption or in which stimulation of bone formation and calcium fixation in the bone is desirable in which an effective amount of an agent of the invention, or a pharmaceutically-acceptable and cleavable ester, or acid addition salt thereof is administered to a patient in need of such treatment, especially in an amount effective in said treatment.

In a yet further aspect the invention includes a pharmaceutical composition for preventing or treating bone conditions which are associated with increased calcium depletion or resorption or in which stimulation of bone formation and calcium fixation in the bone is desirable comprising an agent of the invention, or a pharmaceutically-acceptable and -cleavable ester, or acid addition salt thereof, in admixture with a pharmaceutically acceptable excipient, diluent or carrier.

In a yet further aspect the invention includes the use of an agent of the invention in the manufacture of a medicament for the treatment or prevention of a bone condition, and a compound of the formula I for use in such treatment.

The compounds of the Examples herein below generally have $IC_{50}$ values below 1 μM. For instance, the compounds of Examples 1, 6, 8, 10, 14, 18, 20, 24, 34 and 59 have $IC_{50}$ values of 0.083, 0.139, 0.024, 0.028, 0.042, 0.047, 0.203, 0.083, 0.141, 0.236 μM respectively.

The kinase activity of ALK5 is assessed by measuring radiolabelled phosphate [33P] incorporation in to the generic substrate, casein. The kinase domain of human ALK5 (amino acids 200-503) is fused to an N-terminal histidine tag. The kinase activity of ALK5 is rendered constitutive via point mutation at amino acid 204 (threonine to aspartate modification, ALK5 T204D) and the kinase construct is engineered to be expressed from a baculovirus expression construct in insect cells. The purified, recombinantly-expressed histidine-tagged ALK5 T204D protein is dissolved at 5.4 mg/ml in 50 mM Tris-HCl pH 8.0, 150 mM NaCl, 5 mM DTT. ALK5 T204D is dissolved to 2.5 μg/ml in assay buffer (Assay buffer: 20 mM Tris-HCl pH 7.4, 10 mM $MgCl_2$, 2 mM $MnCl_2$) on the day of use.

Test compounds and reference compounds are dissolved in assay buffer without DTT containing 5% (v/v) DMSO. Stock solutions of test and reference compounds are diluted in assay buffer with DTT (1.25 mM) containing 4.5% (v/v) DMSO. 10 μl of test or reference compound are added to the corresponding wells of 96 well U-bottomed plate. Total enzyme activity is determined by measuring ALK5 T204D activity in the absence of ALK5 kinase inhibitor reference compounds. Non-specific binding (NSB) is determined by measuring the activity of ALK5 T204D in the presence of ALK5 kinase inhibitor reference compounds. 10 μl of dephosphorylated casein stock solution (dephosphorylated casein is dissolved in $ddH_2O$ at 20 mg/ml) is added per well (200 μg/well final assay concentration). 20 μl of ALK5 T204D (2.5 μg/ml solution) is added per well (50 ng/well final assay concentration). The plates are left to incubate at room temperature for 10 minutes.

10 μl of ATP mix is added to the well to initiate the reaction (0.66 nM [$^{33}$P]ATP/1 μM unlabelled ATP/well final assay concentration). The ATP mix is prepared as follows, unlabelled ATP (3 mM) is dissolved in $ddH_2O$ and pH adjusted to 7.4. The stock concentration of [$^{33}$P]ATP is 10 μCi/μl. The corresponding volume of [$^{33}$P]ATP is added to unlabelled ATP solution such that the final assay concentration per well is 0.1 μCi. Following addition of the ATP mix, the plates are incubated at room temperature for 50 minutes. The kinase reaction is terminated by the addition of 50 μL Stop Buffer (20 mM Tris-HCl pH 7.4, 10 mM EDTA).

75 μl/well from the reaction plate is transferred to a Multiscreen-IP plate (MultiScreen-IP plates are prepared by added 50 μL of 70% (v/v) ethanol per well and incubated for 5 minutes at room temperature. The ethanol is removed by aspiration via a MultiScreen HTS Vacuum Manifold unit (Millipore, Cat no: MSVMHT500). The plates are washed twice by adding 200 μl/well ddH₂O). The MultiScreen-IP plate is incubated at room temperature for 30 minutes to allowing binding of casein to the plate. The MultiScreen-IP plates are washed three times by adding 200 μl/well 100 mM phosphoric acid solution and the gasket is carefully removed from the back of the MultiScreen-IP plate and the plate dried in the oven for 30 minutes. The MultiScreen-IP plate is backsealed, 50 μL of Microscint™ 20 is added, then the plates are topsealed and radiolabelled casein detected and quantified on a TopCount™ plate-reader using the $^{33}$P scintillation protocol.

The agents of the invention are also useful as co-therapeutic agents for use in combination with other drug substances such as anti-inflammatory, bronchodilatory, antihistamine, decongestant or anti-tussive drug substances, particularly in the treatment of obstructive or inflammatory airways diseases such as those mentioned hereinbefore, for example as potentiators of therapeutic activity of such drugs or as a means of reducing required dosaging or potential side effects of such drugs. An agent of the invention may be mixed with one or more other drug substances in a fixed pharmaceutical composition or it may be administered separately, before, simultaneously with or after the other drug substance(s).

Such anti-inflammatory drugs include steroids, in particular glucocorticosteroids such as budesonide, beclamethasone dipropionate, fluticasone propionate, ciclesonide or mometasone furoate, or steroids described in WO 02/88167, WO 02/12266, WO 02/100879, WO 02/00679 [Novartis] (especially those of Examples 3, 11, 14, 17, 19, 26, 34, 37, 39, 51, 60, 67, 72, 73, 90, 99 and 101), WO 03/35668, WO 03/48181, WO 03/62259, WO 03/64445, WO 03/72592, WO 04/39827 and WO 04/66920; non-steroidal glucocorticoid receptor agonists, such as those described in DE 10261874, WO 00/00531, WO 02/10143, WO 03/82280, WO 03/82787, WO 03/86294, WO 03/104195, WO 03/101932, WO 04/05229, WO 04/18429, WO 04/19935, WO 04/26248 and WO 05/05452; LTB4 antagonists such as BIIL 284, CP-195543, DPC11870, LTB4 ethanolamide, LY 293111, LY 255283, CGS025019C, CP-195543, ONO-4057, SB 209247, SC-53228 and those described in U.S. Pat. No. 5,451,700 and WO 04/108720; LTD4 antagonists such as montelukast, pranlukast, zafirlukast, accolate, SR2640, Wy-48,252, ICI 198615, MK-571, LY-171883, Ro 24-5913 and L-648051; Dopamine receptor agonists such as cabergoline, bromocriptine, ropinirole and 4-hydroxy-7-[2-[[2-[[3-(2-phenylethoxy)-propyl]sulfonyl]ethyl]amino]ethyl]-2(3H)benzothiazolone and pharmaceutically acceptable salts thereof (the hydrochloride being Viozan®-AstraZeneca); PDE4 inhibitors such as cilomilast (Ariflo® GlaxoSmithKline), Roflumilast (Byk Gulden), V-11294A (Napp), BAY19-8004 (Bayer), SCH-351591 (ScheringPlough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo), GRC 3886 (Oglemilast, Glenmark), WO 92/19594, WO 93/19749, WO 93/19750, WO 93/19751, WO 99/16766, WO 01/13953, WO 03/104204, WO 03/104205, WO 04/000814, WO 04/000839 and WO 04/005258 (Merck), WO 04018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607, WO 04/037805, WO 04/063197, WO 04/103998, WO 04/111044, WO 05012252, WO 05012253, WO 05/013995, WO 05/030212, WO 05/030725, WO 05/087744, WO 05/087745, WO 05/087749 and WO 05/090345 as well as those described in WO 98/18796 and WO 03/39544. A2a agonists such as those described in EP 409595A2, EP 1052264, EP 1241176, WO 94/17090, WO 96/02543, WO 96/02553, WO 98/28319, WO 99/24449, WO 99/24450, WO 99/24451, WO 99/38877, WO 99/41267, WO 99/67263, WO 99/67264, WO 99/67265, WO 99/67266, WO 00/23457, WO 00/77018, WO 00/78774, WO 01/23399, WO 01/27130, WO 01/27131, WO 01/60835, WO 01/94368, WO 02/00676, WO 02/22630, WO 02/96462, WO 03/086408, WO 04/039762, WO 04/039766, WO 04/045618 and WO 04/046083; and A2b antagonists such as those described in WO 02/42298 and WO 03/042214.

Such bronchodilatory drugs include beta-2 adrenoceptor agonists. Suitable beta-2 adrenoceptor agonists include albuterol (salbutamol), metaproterenol, terbutaline, salmeterol, fenoterol, procaterol, and especially, formoterol, carmoterol, GSK159797 and pharmaceutically acceptable salts thereof, and compounds (in free or salt or solvate form) of formula I of WO 0075114, which document is incorporated herein by reference, preferably compounds of the Examples thereof, especially a compound of formula

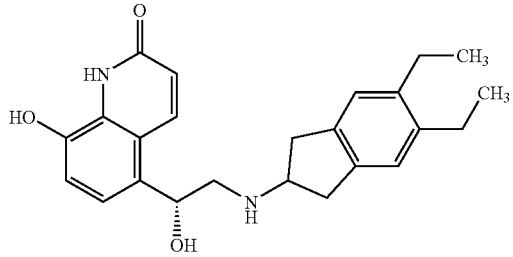

and pharmaceutically acceptable salts thereof, as well as compounds (in free or salt or solvate form) of formula I of WO 04/16601 or of formula I of WO 04/087142. Further suitable β-2-adrenoreceptor agonists include compounds, such as those described in and also compounds of EP 147719, EP 1440966, EP 1460064, EP 1477167, EP 1574501, JP 05025045, JP 2005187357, US 2002/0055651, US 2004/0242622, US 2004/0229904, US 2005/0133417, US 2005/5159448, US 2005/5159448, US 2005/171147, US 2005/182091, US 2005/182092, US 2005/209227, US 2005/256115, US 2005/277632, US 2005/272769, US 2005/239778, US 2005/215542, US 2005/215590, US 2006/19991, US 2006/58530, WO 93/18007, WO 99/64035, WO 01/42193, WO 01/83462, WO 02/66422, WO 02/70490, WO 02/76933, WO 03/24439, WO 03/42160, WO 03/42164, WO 03/72539, WO 03/91204, WO 03/99764, WO 04/16578, WO 04/22547, WO 04/32921, WO 04/33412, WO 04/37768, WO 04/37773, WO 04/37807, WO 04/39762, WO 04/39766, WO 04/45618 WO 04/46083, WO 04/80964, WO 04/087142, WO 04/89892, WO 04/108675, WO 04/108676, WO 05/33121, WO 05/40103, WO 05/44787, WO 05/58867, WO 05/65650, WO 05/66140, WO 05/70908, WO 05/74924, WO 05/77361, WO 05/90288, WO 05/92860, WO 05/92887, WO 05/90287, WO 05/95328, WO 05/102350, WO 06/56471, WO 06/74897 or WO 06/8173.

Such bronchodilatory drugs also include other anticholinergic or antimuscarinic agents, in particular ipratropium bromide, oxitropium bromide, tiotropium salts, glycopyrrolate, CHF 4226 (Chiesi) and SVT-40776, but also those described in EP 424021, U.S. Pat. Nos. 3,714,357, 5,171,744, US 2005/171147, US 2005/182091, WO 01/04118, WO 02/00652, WO 02/51841, WO 02/53564, WO 03/00840, WO 03/33495, WO 03/53966, WO 03/87094, WO 04/18422, WO 04/05285, WO 04/96800, WO 05/77361 and WO 06/48225.

Suitable dual anti-inflammatory and bronchodilatory drugs include dual beta-2 adrenoceptor agonist/muscarinic antagonists such as those disclosed in US 2004/0167167, US 2004/0242622, US 2005/182092, US 2005/256114, US 2006/35933, WO 04/74246, WO 04/74812, WO 04/89892 and WO 06/23475.

Suitable antihistamine drug substances include cetirizine hydrochloride, levocetirizine, acetaminophen, clemastine fumarate, promethazine, loratidine, desloratidine, diphenhydramine and fexofenadine hydrochloride, activastine, astemizole, azelastine, dimetinden, ebastine, epinastine, levocabastine, mizolastine and tefenadine as well as those disclosed in WO 03/099807, WO 04/026841 and JP 2004107299.

According to a further embodiment of the invention, the agents of the Invention may be employed as adjunct or adjuvant to other therapy, e.g. a therapy using a bone resorption inhibitor, for example as in osteoporosis therapy, in particular a therapy employing calcium, a calcitonin or an analogue or derivative thereof, e.g. salmon, eel or human calcitonin, a steroid hormone, e.g. an estrogen, a partial estrogen agonist or estrogen-gestagen combination, a SERM (Selective Estrogen Receptor Modulator) e.g. raloxifene, Iasofoxifene, TSE-424, FC1271, Tibolone (Livial A), vitamin D or an analog thereof or PTH, a PTH fragment or a PTH derivative e.g. PTH (1-84), PTH (1-34), PTH (1-36), PTH (1-38), PTH (1-31) NH2 or PTS 893.

The agents of the invention may further be employed in combination with human insulin-like growth factor1 or IGF1, however formulated or stabilized, such as IPLEX™ as developed by Insmed Inc or as described in US 2006/0166328.

In accordance with the foregoing, the present invention also provides a method for the treatment of an obstructive or inflammatory airways disease which comprises administering to a subject, particularly a human subject, in need thereof an agent of the invention, or a pharmaceutically acceptable salt or solvate thereof, as hereinbefore described. In another aspect, the invention provides an agent of the invention, or a pharmaceutically acceptable salt or solvate thereof, as hereinbefore described for use in the preparation of a medicament for the treatment of an obstructive or inflammatory airways disease.

The agents of the invention may be administered by any appropriate route, e.g. orally, for example in the form of a tablet or capsule; parenterally, for example intravenously; topically to the skin, for example in the treatment of psoriasis; intranasally, for example in the treatment of hay fever; or, preferably, by inhalation, particularly in the treatment of obstructive or inflammatory airways diseases. In particular, the agents of the invention may be delivered as an inhalable formulation for the treatment of COPD and asthma.

In a further aspect, the invention also provides a pharmaceutical composition comprising an agent of the invention in free form or in the form of a pharmaceutically acceptable salt or solvate thereof, optionally together with a pharmaceutically acceptable diluent or carrier therefor. Such compositions may be prepared using conventional diluents or excipients and techniques known in the galenic art. Thus oral dosage forms may include tablets and capsules. Formulations for topical administration may take the form of creams, ointments, gels or transdermal delivery systems, e.g. patches. Compositions for inhalation may comprise aerosol or other atomizable formulations or dry powder formulations. Where the inhalable form of the active ingredient is an aerosol composition, the inhalation device may be an aerosol vial provided with a valve adapted to deliver a metered dose, such as 10 to 1000, e.g. 25 to 50 µl, of the composition, i.e. a device known as a metered dose inhaler. Suitable such aerosol vials and procedures for containing within them aerosol compositions under pressure are well known to those skilled in the art of inhalation therapy. For example, an aerosol composition may be administered from a coated can, for example as described in EP-A-0642992. Where the inhalable form of the active ingredient is a nebulizable aqueous, organic or aqueous/organic dispersion, the inhalation device may be a known nebulizer, for example a conventional pneumatic nebulizer such as an airjet nebulizer, or an ultrasonic nebulizer, which may contain, for example, from 1 to 50 ml, commonly 1 to 10 ml, of the dispersion; or a hand-held nebulizer, sometimes referred to as a soft mist or soft spray inhaler, for example an electronically controlled device such as an AERx (Aradigm, US) or Aerodose (Aerogen), or a mechanical device such as a RESPIMAT (Boehringer Ingelheim) nebulizer which allows much smaller nebulized volumes, e.g. 10 to 100 µl, than conventional nebulizers. Where the inhalable form of the active ingredient is the finely divided particulate form, the inhalation device may be, for example, a dry powder inhalation device adapted to deliver dry powder from a capsule or blister containing a dry powder comprising a dosage unit of (A) and/or (B) or a multidose dry powder inhalation (MDPI) device adapted to deliver, for example, 3-25 mg of dry powder comprising a dosage unit of (A) and/or (B) per actuation. The dry powder composition preferably contains a diluent or carrier, such as lactose, and a compound that helps to protect against product performance deterioration due to moisture e.g. magnesium stearate. Suitable such dry powder inhalation devices include devices disclosed in U.S. Pat. No. 3,991,761 (including the AEROLIZER™ device), WO 05/113042, WO 97/20589 (including the CERTIHALER™ device), WO 97/30743 (including the TWISTHALER™ device) and WO 05/37353 (including the GYROHALER™ device).

The invention also includes (A) an agent of the invention in free form, or a pharmaceutically acceptable salt or solvate thereof, in inhalable form; (B) an inhalable medicament comprising such a compound in inhalable form together with a pharmaceutically acceptable carrier in inhalable form; (C) a pharmaceutical product comprising such a compound in inhalable form in association with an inhalation device; and (D) an inhalation device containing such a compound in inhalable form.

Dosages of agents of the invention employed in practising the present invention will of course vary depending, for example, on the particular condition to be treated, the effect desired and the mode of administration. In general, suitable daily dosages for administration by inhalation are of the order of 0.0001 to 30 mg/kg, typically 0.01 to 10 mg per patient, while for oral administration suitable daily doses are of the order of 0.01 to 100 mg/kg.

The invention is illustrated by the following Examples.

EXAMPLES

The invention is illustrated by the following Examples.

Especially preferred compounds of the present invention include compounds of formula I

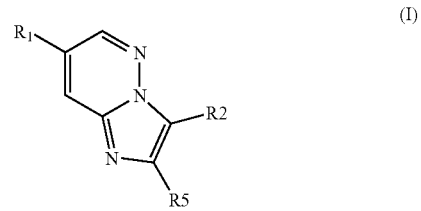

(I)

where $R_1$, $R_2$ and $R_5$ are as shown in Table I below. The method of preparation being described hereinafter.

TABLE 1

| Ex. | R₁ | R₂ | R₅ | MH+ |
|---|---|---|---|---|
| 1 | 3-methyl-N-methylbenzamide | 4-methyl-2-phenylpyridine | H | 406 |
| 2 | 3-methyl-N-methylbenzamide | 4-methyl-2-(furan-3-yl)pyridine | H | 396 |
| 3 | 3-methyl-N-methylbenzamide | 3-methyl-1-(1H-pyrazol-1-yl)phenyl | H | 395 |
| 4 | 3-methyl-N-methylbenzamide | 4-methyl-2-(3-fluorophenyl)pyridine | H | 424 |
| 5 | 3-methyl-N-methylbenzamide | 4-methyl-2-(furan-2-yl)pyridine | H | 396 |
| 6 | 3-methyl-N-methylbenzamide | 4-methyl-2-(4-fluorophenyl)pyridine | H | 424 |
| 7 | 3-methyl-N-methylbenzamide | 3-methyl-N-methylbenzamide | H | 386 |
| 8 | 3-methylphenol | 3-methyl-1-(1H-pyrazol-1-yl)phenyl | H | 354 |
| 9 | 3-methylphenol | 4-methyl-2-methoxyphenol | H | 334 |

TABLE 1-continued
| Ex. | R₁ | R₂ | R₅ | MH+ |
|---|---|---|---|---|
| 10 | 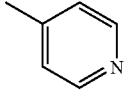 | 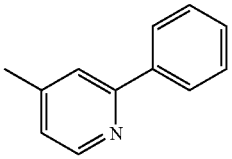 | H | 350 |
| 11 | 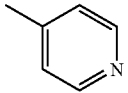 | 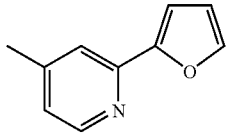 | H | 340 |
| 12 | 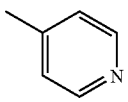 | 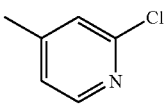 | H | 308 |
| 13 | 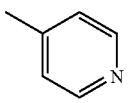 | 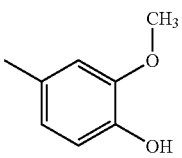 | H | 319 |
| 14 | 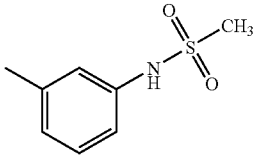 | 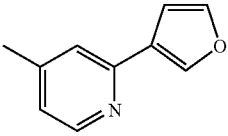 | H | 432 |
| 15 | 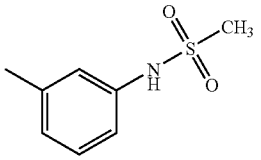 | 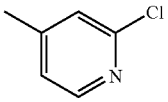 | H | 400 |
| 16 | 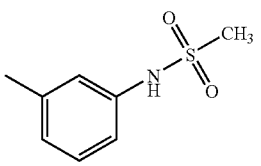 | 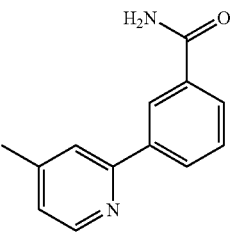 | H | 485 |
| 17 | 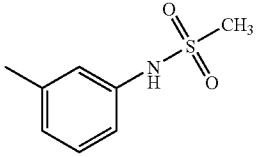 |  | H | 408 |
| 18 | 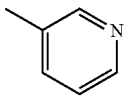 | 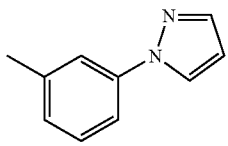 | H | 339 |

TABLE 1-continued
| Ex. | R₁ | R₂ | R₅ | MH+ |
|---|---|---|---|---|
| 19 | 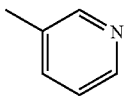 | 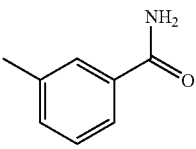 | H | 316 |
| 20 | 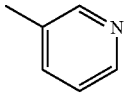 | 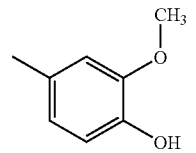 | H | 319 |
| 21 | 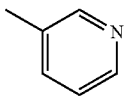 | 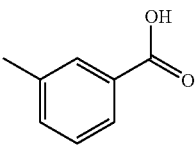 | H | 317 |
| 22 | 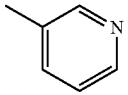 | 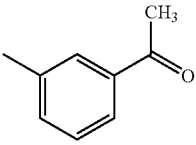 | H | 315 |
| 23 | 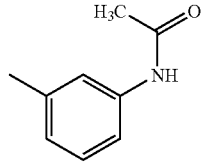 | 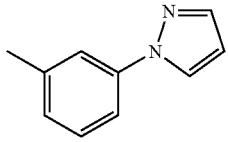 | H | 395 |
| 24 | 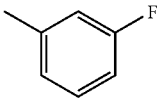 | 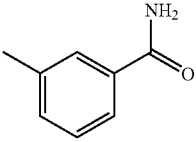 | H | 333 |
| 25 | 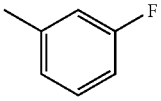 | 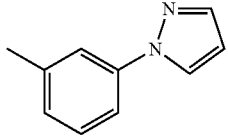 | H | 356 |
| 26 | 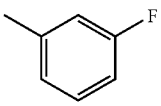 | 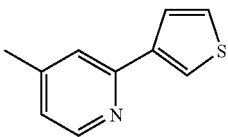 | H | 373 |
| 27 | 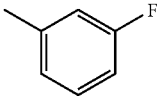 | 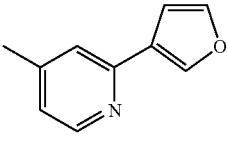 | H | 357 |
| 28 | 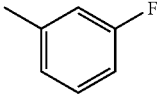 | 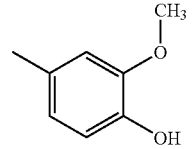 | H | 336 |

TABLE 1-continued
| Ex. | R₁ | R₂ | R₅ | MH+ |
|---|---|---|---|---|
| 29 | 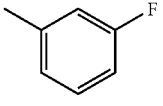 | 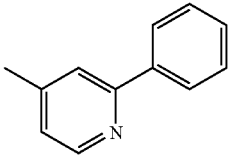 | H | 367 |
| 30 | 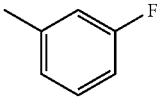 | 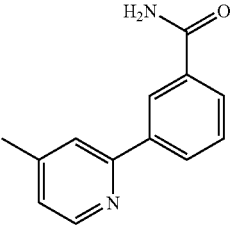 | H | 410 |
| 31 | 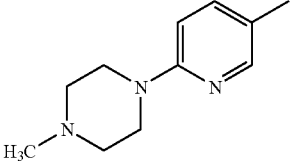 | 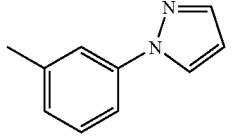 | H | 437 |
| 32 | 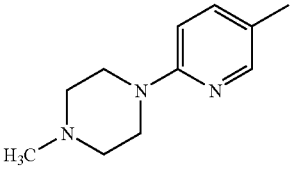 | 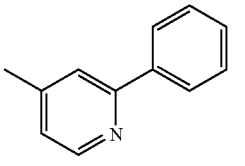 | H | 448 |
| 33 | 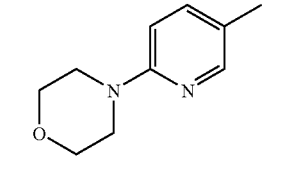 | 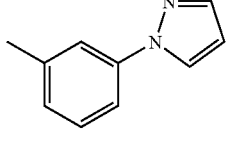 | H | 424 |
| 34 | 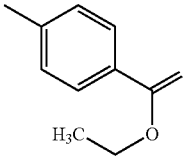 | 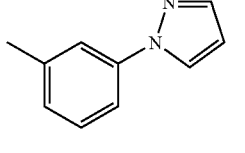 | H | 410 |
| 35 | 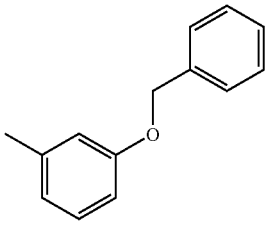 | 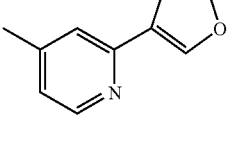 | H | 445 |
| 36 | 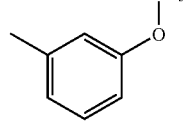 | 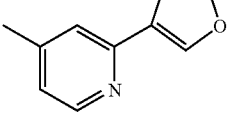 | H | 369 |

TABLE 1-continued
| Ex. | R₁ | R₂ | R₅ | MH+ |
|---|---|---|---|---|
| 37 | 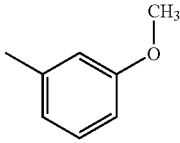 | 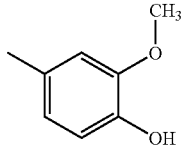 | H | 348 |
| 38 | 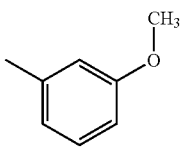 | 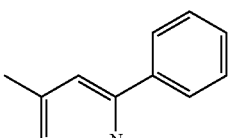 | H | 379 |
| 39 | 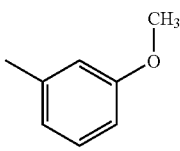 | 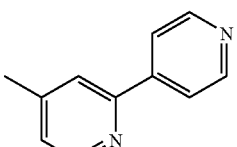 | H | 380 |
| 40 | 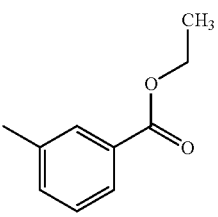 | 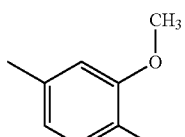 | H | 390 |
| 41 | 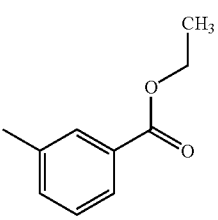 | 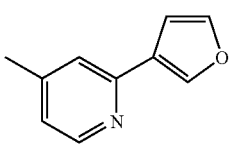 | H | 411 |
| 42 | 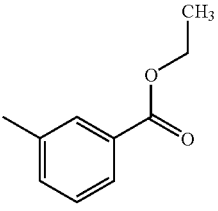 | 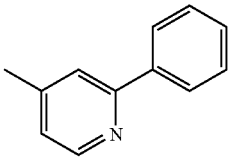 | H | 421 |
| 43 | 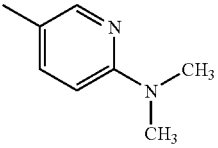 | 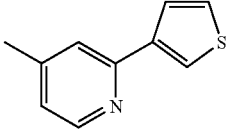 | H | 399 |
| 44 | 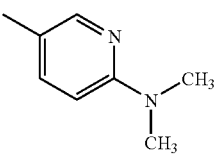 | 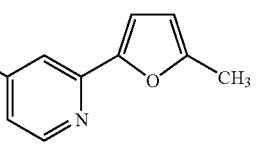 | H | 397 |

TABLE 1-continued
| Ex. | R₁ | R₂ | R₅ | MH+ |
|---|---|---|---|---|
| 45 | 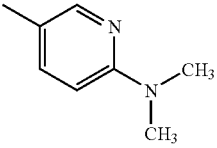 | 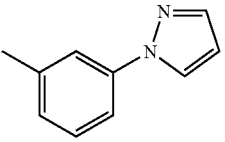 | H | 382 |
| 46 |  | 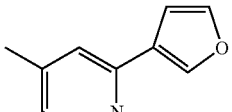 | H | 383 |
| 47 |  | 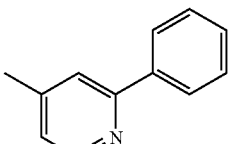 | H | 393 |
| 48 | 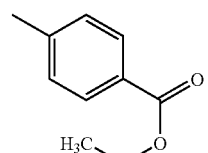 | 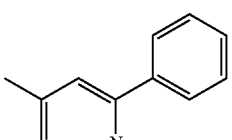 | H | 421 |
| 49 | 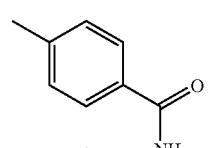 | 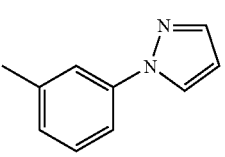 | H | 425 |
| 50 | 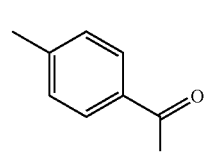 | 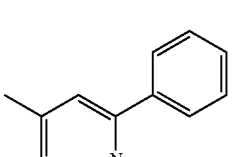 | H | 436 |
| 51 | 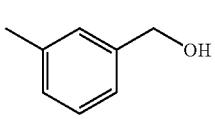 | 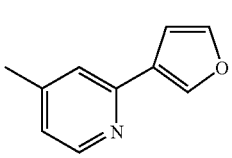 | H | 369 |
| 52 | 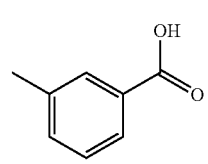 | 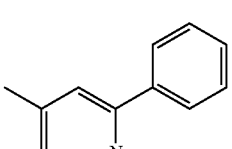 | H | 393 |

TABLE 1-continued

| Ex. | R₁ | R₂ | R₅ | MH+ |
|---|---|---|---|---|
| 53 | 3-carboxyphenyl (benzoic acid, meta-methyl) | 4-methyl-2-methoxy-phenol | H | 362 |
| 54 | 3-(N-methylcarbamoyl)phenyl | 4-methyl-2-phenylpyridin-yl | NH2 | 421 |
| 55 | 3-((3-dimethylamino-propyl)carbamoyl)phenyl | 4-methyl-2-phenylpyridin-yl | H | 477 |
| 56 | 3-((2-piperidin-1-yl-ethyl)carbamoyl)phenyl | 4-methyl-2-phenylpyridin-yl | H | 503 |
| 57 | 3-((2-methylamino-ethyl)(methyl)carbamoyl)phenyl | 4-methyl-2-phenylpyridin-yl | H | 463 |
| 58 | 3-((2-hydroxyethyl)carbamoyl)phenyl | 4-methyl-2-phenylpyridin-yl | H | 436 |

TABLE 1-continued

| Ex. | R₁ | R₂ | R₅ | MH+ |
|---|---|---|---|---|
| 59 | ![structure] H₃C-CH₂CH₂CH₂-NH-C(O)-(3-methylphenyl) | 4-methyl-2-phenylpyridine | H | 448 |
| 60 | piperidine-N-CH₂CH₂CH₂-N-(4-methyl-2-oxopyridin-1-yl) | 3-(pyrazol-1-yl)-methylphenyl | H | 480 |

General Conditions:

Mass spectra are run on an open access Agilent 1100 HPLC/Mass Spectrometer system using atmospheric pressure chemical ionisation. [M+H]⁺ refers to mono-isotopic molecular weights.

Unless otherwise stated, all starting materials are obtained from commercial suppliers and used without further purification.

Abbreviations:

BOP is Benzotriazole-1-yl-oxy-tris-(dimethylamino)-phosphonium hexafluorophosphate, DCM is dichloromethane, DIBAL-His diisobutylaluminum hydride, DME is dimethoxyethane, DMF is dimethylformamide, Et₃N is triethylamine, EtOAc is ethyl acetate, EtOH is ethanol, $H_2O$ is water, HPLC is high performance liquid chromatography, min is minute, mL is milliliter(s), $MgSO_4$ is magnesium sulfate, MeOH is methanol, NaOH is sodium hydroxide, $Na_2CO_3$ is sodium carbonate, NBS is N-bromosuccinimide, NMP is 1-methyl-2-pyrrolidone, NMR is nuclear magnetic resonance, Pd is palladium, $PdCl_2(PPh_3)_2$ is bis(triphenylphosphine)palladium(II) dichloride, $K_2CO_3$ is potassium carbonate, RT is room temperature and SCX is strong cation exchange.

Preparation of Final Compounds

Route A

Example 1

N-Methyl-3-[3-(2-phenyl-pyridin-4-yl)-imidazo[1,2-b]pyridazin-7-yl]-benzamide

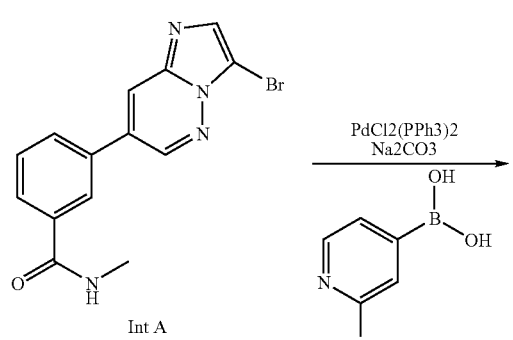

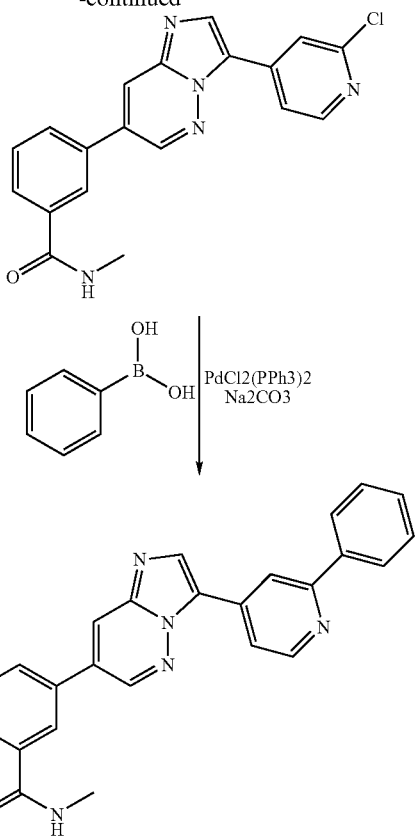

Step A: 3-[3-(2-Chloro-pyridin-4-yl)-imidazo[1,2-b]pyridazin-7-yl]-N-methyl-benzamide To a mixture of 3-(3-Bromo-imidazo-[1,2-b]-pyridazin-7-yl)-N-methyl-benzamide (Intermediate A) (1 eq, 0.353 mmol, 117 mg) and 2-chloropyridine-4-boronic acid (1.2 eq, 0.424 mmol, 66.7 mg) in DME (3 ml) are added water (1 ml) and Na₂CO₃ (2 eq, 0.707 mmol, 87.6 mg). PdCl₂(PPh₃)₂ (0.1 eq, 0.035 mmol, 24.8 mg) is then added and the reaction mixture is heated using microwave radiation at 120° C. for 10 min. At the completion of this time the solvent is removed in vacuo and the reaction mixture is purified by flash column chromatography eluting with 9:1 DCM/MeOH to yield 3-[3-

(2-Chloro-pyridin-4-yl)-imidazo[1,2-b]pyridazin-7-yl]-N-methyl-benzamide as a yellow solid; [M+H]⁺=364

Step B: N-Methyl-3-[3-(2-phenyl-pyridin-4-yl)-imidazo[1,2-b]pyridazin-7-yl]-benzamide 3-[3-(2-Chloro-pyridin-4-yl)-imidazo[1,2-b]pyridazin-7-yl]-N-methyl-benzamide (1 eq, 0.110 mmol, 40 mg) and phenyl boronic acid (1.2 eq, 0.132 mmol, 16.1 mg) are dissolved in DME (1.5 ml) and water (0.5 ml) and Na₂CO₃ (2 eq, 0.22 mmol, 27.3 mg) is added. PdCl₂(PPh₃)₂ (0.1 eq, 0.011 mmol, 7.7 mg) is then added and the reaction mixture is heated using microwave radiation at 120° C. for 10 min. At the completion of this time the solvent is removed in vacuo and the reaction mixture is purified by flash column chromatography eluting with 9:1 DCM/MeOH to yield N-Methyl-3-[3-(2-phenyl-pyridin-4-yl)-imidazo[1,2-b]pyridazin-7-yl]-benzamide as a yellow solid; [M+H]⁺=406

Examples 2 to 48

The following examples, namely,
3-[3-(2-Furan-3-yl-pyridin-4-yl)-imidazo[1,2-b]pyridazin-7-yl]-N-methyl-benzamide (Ex. 2),
3-{3-[2-(3-Fluoro-phenyl)-pyridin-4-yl]-imidazo[1,2-b]pyridazin-7-yl}-N-methyl-benzamide (Ex. 4),
3-[3-(2-Furan-2-yl-pyridin-4-yl)-imidazo[1,2-b]pyridazin-7-yl]-N-methyl-benzamide (Ex. 5),
3-{3-[2-(4-Fluoro-phenyl)-pyridin-4-yl]-imidazo[1,2-b]pyridazin-7-yl}-N-methyl-benzamide (Ex 6),
3-(2-Phenyl-pyridin-4-yl)-7-pyridin-4-yl-imidazo[1,2-b]pyridazine (Ex. 10),
3-(2-Furan-3-yl-pyridin-4-yl)-7-pyridin-4-yl-imidazo[1,2-b]pyridazine (Ex. 11),
N-{3-[3-(2-Furan-3-yl-pyridin-4-yl)-imidazo[1,2-b]pyridazin-7-yl]-phenyl}-methanesulfonamide (Ex. 14),
3-{4-[7-(3-Methanesulfonylamino-phenyl)-imidazo[1,2-b]pyridazin-3-yl]-pyridin-2-yl}-benzamide (Ex. 16),
7-(3-Fluoro-phenyl)-3-(2-thiophen-3-yl-pyridin-4-yl)-imidazo[1,2-b]pyridazine (Ex. 26),
7-(3-Fluoro-phenyl)-3-(2-furan-3-yl-pyridin-4-yl)-imidazo[1,2-b]pyridazine (Ex. 27),
7-(3-Fluoro-phenyl)-3-(2-phenyl-pyridin-4-yl)-imidazo[1,2-b]pyridazine (Ex. 29),
3-{4-[7-(3-Fluoro-phenyl)-imidazo[1,2-b]pyridazin-3-yl]-pyridin-2-yl}benzamide (Ex. 30),
7-[6-(4-Methyl-piperazin-1-yl)-pyridin-3-yl]-3-(2-phenyl-pyridin-4-yl)-imidazo[1,2-b]pyridazine (Ex. 32),
7-(3-Benzyloxy-phenyl)-3-(2-furan-3-yl-pyridin-4-yl)-imidazo[1,2-b]pyridazine (Ex. 35),
3-(2-Furan-3-yl-pyridin-4-yl)-7-(3-methoxy-phenyl)-imidazo[1,2-b]pyridazine (Ex. 36),
7-(3-Methoxy-phenyl)-3-(2-phenyl-pyridin-4-yl)-imidazo[1,2-b]pyridazine (Ex. 38),
4-[7-(3-Methoxy-phenyl)-imidazo[1,2-b]pyridazin-3-yl]-[2,4']bipyridinyl (Ex. 39),
3-[3-(2-Furan-3-yl-pyridin-4-yl)-imidazo[1,2-b]pyridazin-7-yl]-benzoic acid ethyl ester (Ex. 41),
3-[3-(2-Phenyl-pyridin-4-yl)-imidazo[1,2-b]pyridazin-7-yl]-benzoic acid ethyl ester (Ex. 42),
Dimethyl-{5-[3-(2-thiophen-3-yl-pyridin-4-yl)-imidazo[1,2-b]pyridazin-7-yl]-pyridin-2-yl}-amine (Ex. 43),
Dimethyl-(5-{3-[2-(5-methyl-furan-2-yl)-pyridin-4-yl]-imidazo[1,2-b]pyridazin-7-yl}-pyridin-2-yl)-amine (Ex. 44),
{5-[3-(2-Furan-3-yl-pyridin-4-yl)-imidazo[1,2-b]pyridazin-7-yl]-pyridin-2-yl}-amine (Ex. 46),
Dimethyl-{5-[3-(2-phenyl-pyridin-4-yl)-imidazo[1,2-b]pyridazin-7-yl]-pyridin-2-yl}-amine (Ex. 47),
4-[3-(2-Phenyl-pyridin-4-yl)-imidazo[1,2-b]pyridazin-7-yl]-benzoic acid ethyl ester (Ex. 48),
are prepared by an analogous method to N-Methyl-3-[3-(2-phenyl-pyridin-4-yl)-imidazo[1,2-b]pyridazin-7-yl]-benzamide (Ex. 1) by replacing, where appropriate, 3-(3-Bromo-imidazo-[1,2-b]-pyridazin-7-yl)-N-methyl-benzamide (Intermediate A) and using the corresponding boronic acid or boronic ester, namely,
Furan-3-boronic acid (Sigma Aldrich),
3-Fluorophenyl boronic acid (Sigma Aldrich),
Furan-3-boronic acid (Sigma Aldrich),
4-Fluorobenzeneboronic acid (Sigma Aldrich),
3-Bromo-7-pyridin-4-yl-imidazo[1,2-b]pyridazine (Intermediate C) and phenyl boronic acid (Sigma Aldrich),
3-Bromo-7-pyridin-4-yl-imidazo[1,2-b]pyridazine (Intermediate C) and furan-3-boronic acid (Sigma Aldrich),
N-[3-(3-Bromo-imidazo-[1,2-b]pyridazin-7-yl)-phenyl]-methanesulfonamide (Intermediate D) and furan-3-boronic acid (Sigma Aldrich),
N-[3-(3-Bromo-imidazo-[1,2-b]pyridazin-7-yl)-phenyl]-methanesulfonamide (Intermediate D) and 3-aminocarbonyl phenyl boronic acid (Combi Block),
3-Bromo-7-(3-fluoro-phenyl)-imidazo-[1,2-b]pyridazine (Intermediate G) and thiophene-3-boronic acid (Sigma Aldrich),
3-Bromo-7-(3-fluoro-phenyl)-imidazo-[1,2-b]pyridazine (Intermediate G) and furan-3-boronic acid (Sigma Aldrich),
3-Bromo-7-(3-fluoro-phenyl)-imidazo-[1,2-b]pyridazine (Intermediate G) and phenyl boronic acid (Sigma Aldrich),
3-Bromo-7-(3-fluoro-phenyl)-imidazo-[1,2-b]pyridazine (Intermediate G) and 3-aminocarbonyl phenyl boronic acid (Combi Block),
3-Bromo-7-[6-(4-methyl-piperazin-1-yl)-pyridin-3-yl]-imidazo[1,2-b]pyridazine (Intermediate M) and phenyl boronic acid (Sigma Aldrich),
7-(3-Benzyloxy-phenyl)-3-bromo-imidazo-[1,2-b]pyridazine (Intermediate I) and furan-3-boronic acid (Sigma Aldrich),
3-Bromo-7-(3-methoxy-phenyl)-imidazo-[1,2-b]pyridazine (Intermediate J) and furan-3-boronic acid (Sigma Aldrich),
3-Bromo-7-(3-methoxy-phenyl)-imidazo-[1,2-b]pyridazine (Intermediate J) and phenyl boronic acid (Sigma Aldrich),
3-Bromo-7-(3-methoxy-phenyl)-imidazo-[1,2-b]pyridazine (Intermediate J) and 4-pyridine boronic acid (Sigma Aldrich),
3-(3-Bromo-imidazo-[1,2-b]pyridazin-7-yl)-benzoic acid ethyl ester (Intermediate K) and furan-3-boronic acid (Sigma Aldrich),
3-(3-Bromo-imidazo-[1,2-b]pyridazin-7-yl)-benzoic acid ethyl ester (Intermediate K) and phenyl boronic acid (Sigma Aldrich),
[5-(3-Bromo-imidazo-[1,2-b]pyridazin-7-yl)-pyridin-2-yl]-dimethyl-amine (Intermediate L) and thiophene-3-boronic acid (Sigma Aldrich),
[5-(3-Bromo-imidazo-[1,2-b]pyridazin-7-yl)-pyridin-2-yl]-dimethyl-amine (Intermediate L) and 5-methylfuran-2-boronic acid pinacol ester (Sigma Aldrich),
[5-(3-Bromo-imidazo-[1,2-b]pyridazin-7-yl)-pyridin-2-yl]-dimethyl-amine (Intermediate L) and furan-3-boronic acid (Sigma Aldrich),
[5-(3-Bromo-imidazo-[1,2-b]pyridazin-7-yl)-pyridin-2-yl]-dimethyl-amine (Intermediate L) and phenyl boronic acid (Sigma Aldrich), 4-(3-Bromo-imidazo[1,2-b]pyridazin-7-yl)-benzoic acid ethyl ester (Intermediate H) and phenyl boronic acid (Sigma Aldrich), respectively, For the Following Compounds Step B was not Required These examples namely, N-Methyl-3-[3-(3-pyrazol-1-yl-phenyl)-imidazo[1,2-b]pyridazin-7-yl]-benzamide (Ex. 3), 4-[7-(3-Methylcarbamoyl-phenyl)-imidazo[1,2-b]pyridazin-3-yl]-pyridine-2-carboxylic acid methylamide (Ex. 7), 3-[3-(3-Pyrazol-1-yl-phenyl)-imidazo[1,2-b]pyridazin-7-yl]-phenol (Ex. 8), 4-[7-(3-Hydroxy-phenyl)-imidazo[1,2-b]pyridazin-3-yl]-2-methoxy-phenol (Ex. 9), 3-(2-Chloro-pyridin-4-yl)-7-pyridin-4-yl-imidazo[1,2-b]pyridazine (Ex. 12), 2-Methoxy-4-(7-pyridin-4-yl-imidazo[1,2-b]pyridazin-3-yl)-phenol (Ex. 13), N-{3-[3-(2-Chloro-pyridin-4-yl)-imidazo[1,2-b]pyridazin-7-yl]-phenyl}-methanesulfonamide (Ex. 15), 4-[7-(3-Methanesulfonylamino-phenyl)-imidazo[1,2-b]pyridazin-3-yl]-benzamide (Ex. 17), 3-(3-Pyrazol-1-yl-phenyl)-7-pyridin-3-yl-imidazo[1,2-b]pyridazine (Ex. 18), 3-(7-Pyridine-3-yl-imidazo[1,2-b]pyridazin-3-yl)-benzamide (Ex. 19), 2-Methoxy-4-(7-pyridin-3-yl-imidazo[1,2-b]pyridazin-3-yl)-phenol (Ex. 20), 3-(7-Pyridine-3-yl-imidazo[1,2-b]pyridazin-3-yl)-benzoic acid (Ex. 21), 1-[3-(7-Pyridin-3-yl-imidazo[1,2-b]pyridazin-3-yl)-phenyl]-ethanone (Ex. 22), N-{3-[3-(3-Pyrazol-1-yl-phenyl)-imidazo[1,2-b]pyridazin-7-yl]-phenyl}-acetamide (Ex. 23), 3-[7-(3-Fluoro-phenyl)-imidazo[1,2-b]pyridazin-3-yl]-benzamide (Ex. 24), 7-(3-Fluoro-phenyl)-3-(3-pyrazol-1-yl-phenyl)-imidazo[1,2-b]pyridazine (Ex. 25), 4-[7-(3-Fluoro-phenyl)-imidazo[1,2-b]pyridazin-3-yl]-2-methoxy-phenol (Ex. 28), 7-[6-(4-Methyl-piperazin-1-yl)-pyridin-3-yl]-3-[2-(1H-pyrazol-4-yl)-pyridin-4-yl]-imidazo[1,2-b]pyridazine (Ex. 31), 7-(6-Morpholin-4-yl-pyridin-3-yl)-3-(3-pyrazol-1-yl-phenyl)-imidazo[1,2-b]pyridazine (Ex. 33), 4-[3-(3-Pyrazol-1-yl-phenyl)-imidazo[1,2-b]pyridazin-7-yl]-benzoic acid ethyl ester (Ex. 34), 2-Methoxy-4-[7-(3-methoxy-phenyl)-imidazo[1,2-b]pyridazin-3-yl]-phenol (Ex. 37), 3-[3-(4-Hydroxy-3-methoxy-phenyl)-imidazo[1,2-b]pyridazin-7-yl]-benzoic acid ethyl ester (Ex. 40), Dimethyl-{5-[3-(3-pyrazol-1-yl-phenyl)-imidazo[1,2-b]pyridazin-7-yl]-pyridin-2-yl}-amine (Ex. 45), are prepared by an analogous method to N-Methyl-3-[3-(2-phenyl-pyridin-4-yl)-imidazo[1,2-b]pyridazin-7-yl]-benzamide (Ex. 1) by replacing, where appropriate, 3-(3-Bromo-imidazo-[1,2-b]-pyridazin-7-yl)-N-methyl-benzamide (Intermediate A) and using the corresponding boronic acid or boronic ester, namely, 3-(1H-Pyrazol-1-yl)phenyl boronic acid (Chembridge)

3-(N-methylaminocarbonyl)benzene boronic acid (Combi Block)

3-(3-Bromo-imidazo-[1,2-b]pyridazin-7-yl)-phenol (Intermediate B) and 3-(1H-Pyrazol-1-yl)phenyl boronic acid (Chembridge), 3-(3-Bromo-imidazo-[1,2-b]pyridazin-7-yl)-phenol (Intermediate B) and 4-hydroxy-3-methoxyphenylboronic acid pinacol ester (Sigma Aldrich), 3-Bromo-7-pyridin-4-yl-imidazo[1,2-b]pyridazine (Intermediate C), 3-Bromo-7-pyridin-4-yl-imidazo[1,2-b]pyridazine (Intermediate C) and 4-hydroxy-3-methoxyphenylboronic acid pinacol ester (Sigma Aldrich), N-[3-(3-Bromo-imidazo-[1,2-b]pyridazin-7-yl)-phenyl]-methanesulfonamide (Intermediate D), N-[3-(3-Bromo-imidazo-[1,2-b]pyridazin-7-yl)-phenyl]-methanesulfonamide (Intermediate D) and 4-aminocarbonyl phenylboronic acid (Sigma Aldrich), 3-Bromo-7-pyridin-3-yl-imidazo[1,2-b]pyridazine (Intermediate E) and 3-(1H-Pyrazol-1-yl)phenyl boronic acid (Chembridge), 3-Bromo-7-pyridin-3-yl-imidazo[1,2-b]pyridazine (Intermediate E) and 3-aminocarbonyl phenyl boronic acid (Combi Block), 3-Bromo-7-pyridin-3-yl-imidazo[1,2-b]pyridazine (Intermediate E) and 4-hydroxy-3-methoxyphenylboronic acid pinacol ester (Sigma Aldrich), 3-Bromo-7-pyridin-3-yl-imidazo[1,2-b]pyridazine (Intermediate E) and 3-carboxyphenyl boronic acid (Sigma Aldrich), 3-Bromo-7-pyridin-3-yl-imidazo[1,2-b]pyridazine (Intermediate E) and 3-acetylphenylboronic acid (Combi Block), N-[3-(3-Bromo-imidazo-[1,2-b]pyridazin-7-yl)-phenyl]-acetamide (Intermediate F) and 3-(1H-Pyrazol-1-yl) phenyl boronic acid (Chembridge), 3-Bromo-7-(3-fluoro-phenyl)-imidazo-[1,2-b]pyridazine (Intermediate G) and 3-aminocarbonyl phenyl boronic acid (Combi Block), 3-Bromo-7-(3-fluoro-phenyl)-imidazo-[1,2-b]pyridazine (Intermediate G) and 3-(1H-Pyrazol-1-yl)phenyl boronic acid (Chembridge), 3-Bromo-7-(3-fluoro-phenyl)-imidazo-[1,2-b]pyridazine (Intermediate G) and 4-hydroxy-3-methoxyphenylboronic acid pinacol ester (Sigma Aldrich), 3-Bromo-7-[6-(4-methyl-piperazin-1-yl)-pyridin-3-yl]-imidazo[1,2-b]pyridazine (Intermediate M) and 3-(1H-Pyrazol-1-yl)phenyl boronic acid (Chembridge), 3-Bromo-7-(6-morpholin-4-yl-pyridin-3-yl)-imidazo[1,2-b]pyridazine (Intermediate N) and 3-(1H-Pyrazol-1-yl)phenyl boronic acid (Chembridge), 4-(3-Bromo-imidazo-[1,2-b]pyridazin-7-yl)-benzoic acid ethyl ester (Intermediate H) and 3-(1H-Pyrazol-1-yl)phenyl boronic acid (Chembridge), 3-Bromo-7-(3-methoxy-phenyl)-imidazo-[1,2-b]pyridazine (Intermediate J) and 4-hydroxy-3-methoxyphenylboronic acid pinacol ester (Sigma Aldrich), 3-(3-Bromo-imidazo-[1,2-b]pyridazin-7-yl)benzoic acid ethyl ester (Intermediate K) and 4-hydroxy-3-methoxyphenylboronic acid pinacol ester (Sigma Aldrich),

[5-(3-Bromo-imidazo-[1,2-b]pyridazin-7-yl)-pyridin-2-yl]-dimethyl-amine (Intermediate L) and 3-(1H-Pyrazol-1-yl) phenyl boronic acid (Chembridge), respectively, Route B

Example 49

N-(2-Hydroxy-ethyl)-4-[3-(3-pyrazol-1-yl-phenyl)-imidazo-[1,2-b]-pyridazin-7-yl]-benzamide

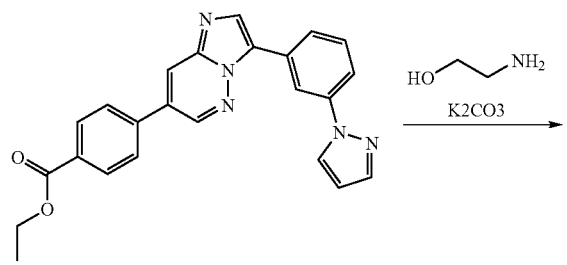

4-[3-(3-Pyrazol-1-yl-phenyl)-imidazo[1,2-b]pyridazin-7-yl]-benzoic acid ethyl ester (Ex. 34) (1 eq, 0.073 mmol, 30 mg) and ethanol amine (10 eq, 0.73 mmol, 0.04 ml) are dissolved in EtOH (2 ml) and $K_2CO_3$ (1.5 eq, 0.11 mmol, 15.1 mg) is added. The reaction mixture is stirred for 5 h at 55° C. The solvent is then removed in vacuo and the reaction is purified by flash column chromatography eluting with 9:1 DCM/MeOH to yield N-(2-Hydroxy-ethyl)-4-[3-(3-pyrazol-1-yl-phenyl)-imidazo-[1,2-b]-pyridazin-7-yl]-benzamide as a yellow solid; $[M+H]^+=425$

Example 50

N-(2-Hydroxy-ethyl)-4-[3-(2-phenyl-pyridin-4-yl)-imidazo-[1,2-b]-pyridazin-7-yl]-benzamide This example is prepared by an analogous method to N-(2-Hydroxy-ethyl)-4-[3-(3-pyrazol-1-yl-phenyl)-imidazo-[1,2-b]-pyridazin-7-yl]-benzamide (Ex. 49) by replacing 4-[3-(3-Pyrazol-1-yl-phenyl)-imidazo[1,2-b]pyridazin-7-yl]-benzoic acid ethyl ester (Ex. 34) with 4-[3-(2-Phenylpyridin-4-yl)-imidazo[1,2-b]pyridazin-7-yl]-benzoic acid ethyl ester (Ex. 48).

Route C

Example 51

{3-[3-(2-Furan-3-yl-pyridin-4-yl)-imidazo[1,2-b]pyridazin-7-yl]-phenyl}-methanol 3-[3-(2-Furan-3-yl-pyridin-4-yl)-imidazo[1,2-b]pyridazin-7-yl]-benzoic acid ethyl ester (Ex. 41) (1 eq, 0.122 mmol, 50 mg) is dissolved in DCM (1 ml) and the reaction mixture is cooled to −70° C. DIBAL-H (1.5 M in THF, 10 eq, 1.22 mmol, 1.74 ml) is then added and the reaction is stirred at this temperature for 3 h. The reaction mixture is then poured in $NaHCO_3$/EtOAc. The organic phase is separated and the aqueous phase is extracted with EtOAc. The combined organic phases are washed with brine, dried over $MgSO_4$, filtered and the solvent is removed in vacuo. The reaction mixture is purified by flash column chromatography eluting with 9:1 DCM/MeOH to afford {3-[3-(2-Furan-3-yl-pyridin-4-yl)-imidazo[1,2-b]pyridazin-7-yl]-phenyl}-methanol as a light brown solid; $[M+H]^+=369$ Route D

Example 52

3-[3-(2-Phenyl-pyridin-4-yl)-imidazo[1,2-b]pyridazin-7-yl]-benzoic acid

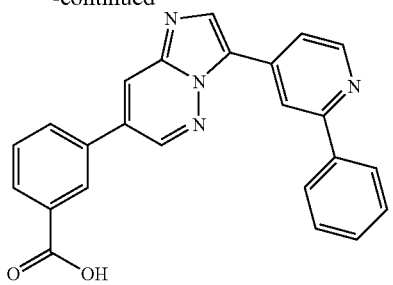

3-[3-(2-Phenyl-pyridin-4-yl)-imidazo[1,2-b]pyridazin-7-yl]-benzoic acid ethyl ester (1 eq, 0.119 mmol, 50 mg) (Ex. 42) is dissolved in THF/H₂O/MeOH (0.5/0.25/0.25 ml) and LiOH (20 eq, 2.38 mmol, 57 mg) is then added and the reaction is stirred at room temperature for 1 h. The reaction mixture is then diluted with MeOH and HCl (1M) is added. The precipitate is filtered and dried to afford 3-[3-(2-Phenyl-pyridin-4-yl)-imidazo[1,2-b]pyridazin-7-yl]-benzoic acid as a yellow solid which did not require further purification; [M+H]⁺=393

Example 53

3-[3-(4-Hydroxy-3-methoxy-phenyl)-imidazo-[1,2-b]-pyridazin-7-yl]-benzoic acid

This example is prepared by an analogous method to 3-[3-(2-Phenyl-pyridin-4-yl)imidazo[1,2-b]pyridazin-7-yl]benzoic acid (Ex. 52) by replacing 3-[3-(2-Phenyl-pyridin-4-yl)-imidazo[1,2-b]pyridazin-7-yl]-benzoic acid ethyl ester (Ex 42) with 3-[3-(4-Hydroxy-3-methoxy-phenyl)-imidazo[1,2-b]pyridazin-7-yl]-benzoic acid ethyl ester (Ex. 40).

Route E

Example 54

3-[(2-Amino-3-(2-phenyl-pyridin-4-yl)-imidazo[1,2-b]pyridazin-7-yl]-N-methyl-benzamide

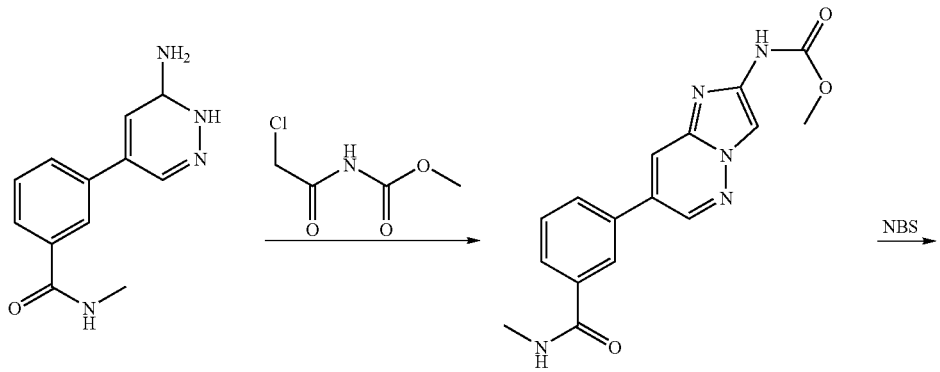

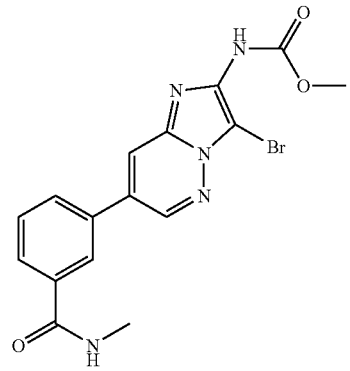

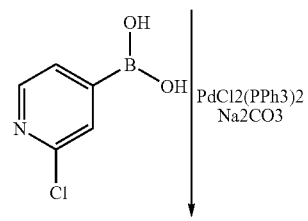

-continued

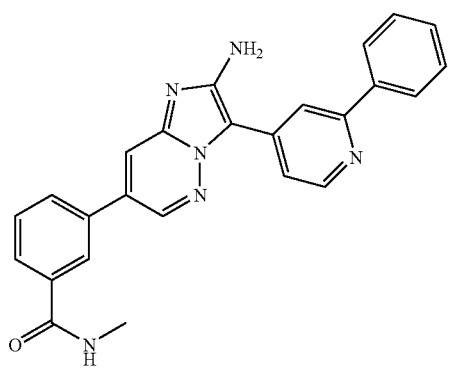 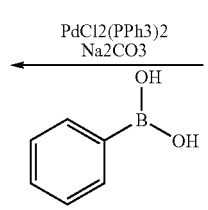 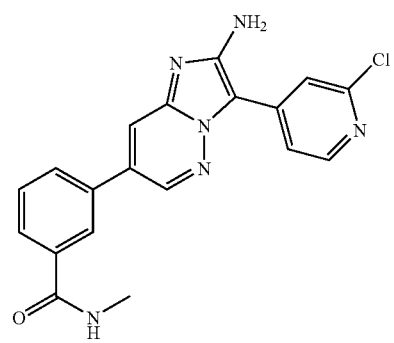

Step A: [7-(3-Methylcarbamoyl-phenyl)-imidazo-[1,2-b]-pyridazin-2-yl]-carbamic acid methyl ester 3-(6-Amino-1,6-dihydro-pyridazin-4-yl)-N-methyl-benzamide (Intermediate A—Step E) (1 eq, 2.74 mmol, 735 mg) is added to a solution of methyl (chloroacetyl)carbamate (1.2 eq, 3.28 mmol, 498 mg) in DMF (30 ml) and the reaction mixture is stirred at 110° C. for 7.5 h. The solvent is then removed in vacuo and the product is purified by flash column chromatography eluting with 9:1 DCM/MeOH to afford [7-(3-Methylcarbamoyl-phenyl)-imidazo-[1,2-b]-pyridazin -2-yl]-carbamic acid methyl ester as a green solid; $[M+H]^+=326$ Step B: [3-Bromo-7-(3-Methylcarbamoyl-phenyl)-imidazo-[1,2-b]-pyridazin-2-yl]-carbamic acid methyl ester

[7-(3-Methylcarbamoyl-phenyl)-imidazo-[1,2-b]-pyridazin-2-yl]-carbamic acid methyl ester (1 eq, 0.167 mmol, 55 mg) is dissolved in DMF (1 ml) at 0° C. and NBS (1.1 eq, 0.184 mmol, 33.8 mg) is added. The reaction mixture is stirred for 1 h at 0° C. and then is diluted with EtOAc. The reaction is washed with NaHCO$_3$ and brine, dried over MgSO$_4$, filtered and evaporated to yield [3-Bromo-7-(3-Methylcarbamoyl-phenyl)-imidazo-[1,2-b]-pyridazin-2-yl]-carbamic acid methyl ester as a brown solid which did not require further purification; $[M+H]^+=406$ Step C: 3-[2-Amino-3-(2-Chloro-pyridin-4-yl)-imidazo-[1,2-b]-pyridazin-7-yl]-N-methyl benzamide

[3-Bromo-7-(3-Methylcarbamoyl-phenyl)-imidazo-[1,2-b]-pyridazin-2-yl]-carbamic acid methyl ester (1 eq, 0.159 mmol, 65 mg) and 2-chloropyridine-4-boronic acid (1.2 eq, 0.191 mmol, 30.1 mg) are dissolved in DME (3 ml) and water (0.75 ml) and Na$_2$CO$_3$ (3 eq, 0.478 mmol, 50.6 mg) is added. PdCl$_2$(PPh$_3$)$_2$ (0.05 eq, 0.008 mmol, 5.59 mg) is then added and the reaction mixture is heated using microwave radiation at 120° C. for 50 min. At the completion of this time the solvent is evaporated and the reaction mixture is dissolved in MeOH, filtered and the solvent is removed in vacuo to yield 3-[2-Amino-3-(2-Chloro-pyridin-4-yl)-imidazo -[1,2-b]-pyridazin-7-yl]-N-methyl benzamide as a yellow solid; $[M+H]^+=379$ Step D: 3-(2-Amino-3-(2-phenyl-pyridin-4-yl)-imidazo[1,2-b]pyridazin-7-yl]-N-methylbenzamide 3-[2-Amino-3-(2-Chloro-pyridin-4-yl)-imidazo-[1,2-b]-pyridazin-7-yl]-N-methyl benzamide (1 eq, 0.146 mmol, 79 mg) and phenyl boronic acid (1.5 eq, 0.219 mmol, 27.5 mg) are dissolved in DME (1.5 ml) and water (0.4 ml) and Na$_2$CO$_3$ (3 eq, 0.438 mmol, 46.4 mg) are added. PdCl$_2$(PPh$_3$)$_2$ (0.05 eq, 0.008 mmol, 5.12 mg) is then added and the reaction mixture is heated using microwave radiation at 120° C. for 15 min. At the completion of this time the solvent is removed in vacuo and the reaction mixture is purified by flash column chromatography eluting with 9:1 DCM/MeOH to yield 3-(2-Amino-3-(2-phenyl-pyridin-4-yl)imidazo [1,2-b] pyridazin-7-yl]-N-methyl-benzamide as a yellow solid; $[M+H]^+=421$ Route F Example 55

N-(3-Dimethylamino-propyl)-3-[3-(2-phenyl-pyridin-4-yl)-imidazo[1,2-b]pyridazin-7-yl]-benzamide

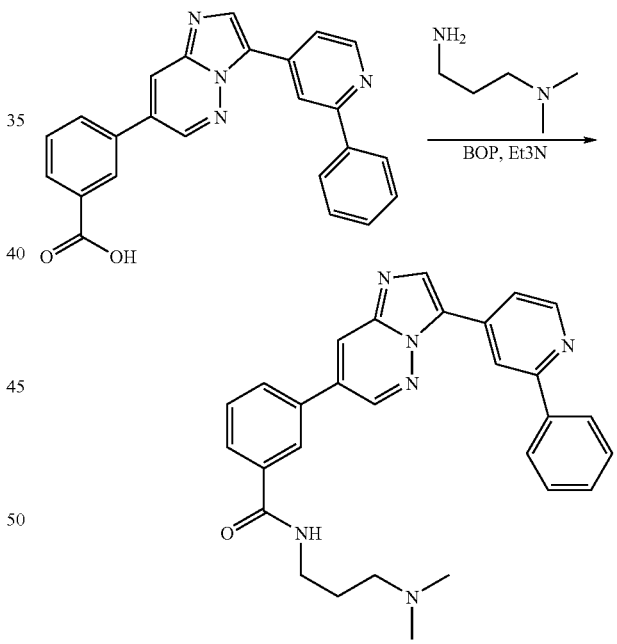

3-[3-(2-Phenyl-pyridin-4-yl)-imidazo[1,2-b]pyridazin-7-yl]-benzoic acid (Ex. 52) (1 eq, 0.127 mmol, 50 mg), 3-dimethylamino-1-propylamine (3.0 eq, 0.38 mmol, 0.049 ml) and triethylamine (1.30 eq, 0.165, 0.023 ml) are dissolved in DCM (2 ml) and BOP (1.30 eq, 0.165 mmol, 73 mg) is added and the reaction mixture is stirred at room temperature for 20 h. At the completion of this time water and EtOAc are added. The organic phase is separated and the aqueous phase is extracted with EtOAc. The combined organic phases are washed with brine, dried over MgSO$_4$, filtered and the solvent is removed in vacuo. The reaction mixture is purified by flash column chromatography eluting with 9:1 DCM/MeOH to afford N-(3-dimethylamino-propyl)-3-[3-(2-phenyl-pyridin-4-yl)-imidazo[1,2-b]pyridazin-7-yl]-benzamide as a light yellow solid; [M+H]$^+$=477

Examples 56 to 59

These examples namely,
3-[3-(2-Phenyl-pyridin-4-yl)-imidazo[1,2-b]pyridazin-7-yl]-N-(2-piperidin-1-yl-ethyl)-benzamide (Ex. 56),
N-Methyl-N-(2-methylamino-ethyl)-3-[3-(2-Phenyl-pyridin-4-yl)-imidazo[1,2-b]pyridazin-7-yl]-benzamide (Ex. 57),
N-(2-Hydroxy-ethyl)-3-[3-(2-Phenyl-pyridin-4-yl)-imidazo[1,2-b]pyridazin-7-yl]-benzamide (Ex. 58),
N-Butyl-3-[3-(2-Phenyl-pyridin-4-yl)-imidazo[1,2-b]pyridazin-7-yl]-benzamide (Ex. 59), are prepared by an analogous method to N-(3-Dimethylamino-propyl)-3-[3-(2-phenyl-pyridin -4-yl)-imidazo[1,2-b]pyridazin-7-yl]-benzamide (Ex. 55) by replacing 3-dimethylamino-1-propylamine with the corresponding amine, namely,
1-(2-Aminoethyl)piperidine (Sigma Aldrich),
N,N'-Dimethylethylenediamine (Sigma Aldrich),
2-Aminoethanol,
Butylamine (Sigma Aldrich), respectively, Route G Example 60

1-(3-Piperidin-1-yl-propyl)-4-[3-(3-pyrazol-1-yl-phenyl)-imidazo[1,2-b]pyridazin-7-yl]-1H-pyridin -2-one

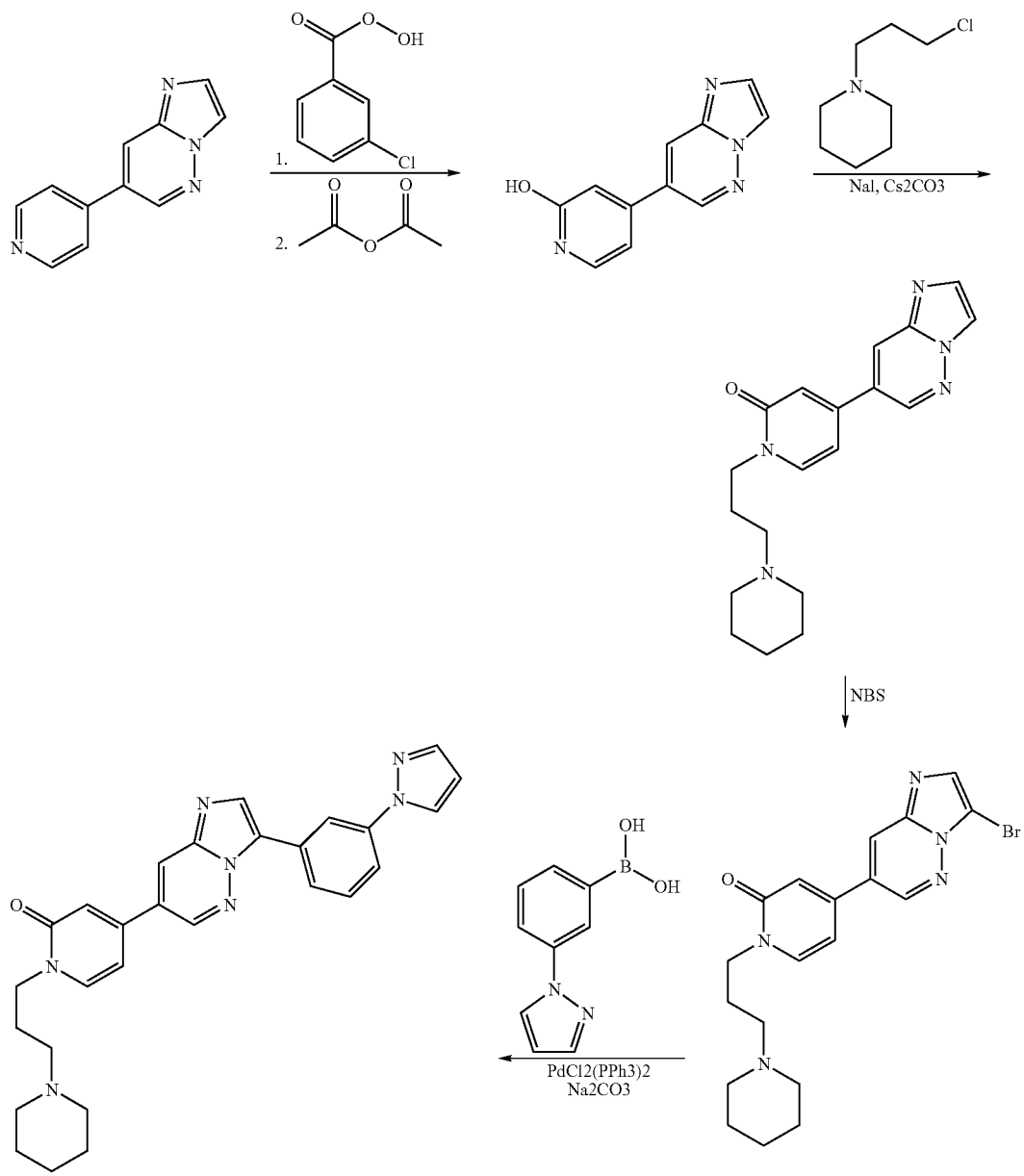

Step A: 4-Imidazo[1,2-b]pyridazin-7-yl-pyridin-2-ol

7-Pyridin-4-yl-imidazo[1,2-b]pyridazine (Intermediate A—Step F) (1 eq, 0.80 mmol, 158 mg) is dissolved in $CH_2Cl_2$ (7 ml) and cooled to 0° C. 3-Chloroperoxybenzoic acid (1.2 eq, 0.97 mmol, 217 mg) is then added and the reaction mixture is stirred at it for 24 h. The yellow suspension is then filtered and the mixture is purified by flash column chromatography eluting with $CH_2Cl_2$/MeOH (80:20) to give 7-(1-oxy-pyridin-4-yl)-imidazo[1,2-b]pyridazine as a light yellow solid. The obtained 7-(1-oxy-pyridin-4-yl)-imidazo[1,2-b]pyridazine (1 eq, 0.33 mmol, 70 mg) is dissolved in acetic anhydride (40 eq, 13.2 mmol, 1.35 g) and they are heated at 140° C. for 12 h to give a black solution. The solution is concentrated to dryness and is dissolved in MeOH(2 ml). NH4OH (aqueous 25%, 0.2 ml) is then added and the mixture is stirred for a further 2 h. The solution is then concentrated to dryness and the mixture is purified by flash column chromatography eluting with CH2Cl2/MeOH (80:20) to afford 4-imidazo[1,2-b]pyridazin-7-yl-pyridin-2-ol as a light yellow oil; $[M+H]^+=197$ Step B: 4-Imidazo[1,2-b]pyridazin-7-yl-1-(3-piperidin-1-yl-propyl)-1H-pyridin-2-one 4-Imidazo[1,2-b]pyridazin-7-yl-pyridin-2-ol (1 eq, 0.17 mmol, 36 mg), 1-(3-chloropropyl)piperidine monohydrochloride (1.5 eq, 0.255 mmol, 52 mg) and sodium iodide (1.5 eq, 0.254 mmol, 37.9 mg) are dissolved in DMF (1 ml) and heated at 60° C. for 16 h to give a black solution. The reaction mixture is then poured into aq. sat. NaHCO3 and the organic phase is extracted with CH2Cl2. The organic phase is washed with brine, dried over MgSO4, filtered and evaporated to dryness to afford 4-imidazo[1,2-b]pyridazin-7-yl-1-(3-piperidin-1-yl-propyl)-1H-pyridin-2-one; $[M+H]^+=338$ Step C: 4-(3-Bromo-imidazo[1,2-b]pyridazin-7-yl)-1-(3-piperidin-1-yl-propyl)-1H-pyridin-2-one 4-Imidazo[1,2-b]pyridazin-7-yl-1-(3-piperidin-1-yl-propyl)-1H-pyridin-2-one (1 eq, 0.122 mmol, 41.3 mg) is dissolved in DMF (10 ml) and N-bromosuccinimide (1.1 eq, 0.135 mmol, 24.2 mg) is added. The reaction mixture is then stirred at 0° C. for 30 min. The reaction is diluted with EtOAc and washed with NaHCO3 and brine. The organic phase is then dried over MgSO4, filtered and evaporated to dryness to give 4-(3-bromo-imidazo[1,2-b]pyridazin-7-yl)-1-(3-piperidin-1-yl-propyl)-1H-pyridin-2-one as a brown solid which did not require any further purification; $[M+H]^+=417$ Step D: 1-(3-Piperidin-1-yl-propyl)-4-[3-(3-pyrazol-1-yl-phenyl)-imidazo[1,2-b]pyridazin-7-yl]-1H-pyridin-2-one 4-(3-Bromo-imidazo[1,2-b]pyridazin-7-yl)-1-(3-piperidin-1-yl-propyl)-1H-pyridin-2-one (1.0 eq, 0.096 mmol, 40 mg), [3-(1H-pyrazol-1-yl)phenyl]boronic acid (1.50 eq, 0.144 mmol, 28.5 mg) and Na2CO3 (2.0 eq, 0.192 mmol, 20.4 mg) are dissolved in DME/H2O (3/1 ml) and PdCl2(PPh3)2 (0.1 eq, 0.0096 mmol, 6.74 mg) is added. The reaction mixture is then heated in a microwave at 120° C. for 10 min. At the completion of this time the solvent is removed in vacuo and the product is purified by flash column chromatography eluting with CH2Cl2/MeOH (80:20) to give 1-(3-piperidin-1-yl-propyl)-4-[3-(3-pyrazol-1-yl-phenyl)imidazo[1,2-b]pyridazin-7-yl]-1H-pyridin-2-one as a yellow solid; $[M+H]^+=480$ (1) Preparation of Intermediate Compounds Intermediate A 3-(3-Bromo-imidazo-[1,2-b]-pyridazin-7-yl)-N-methyl-benzamide

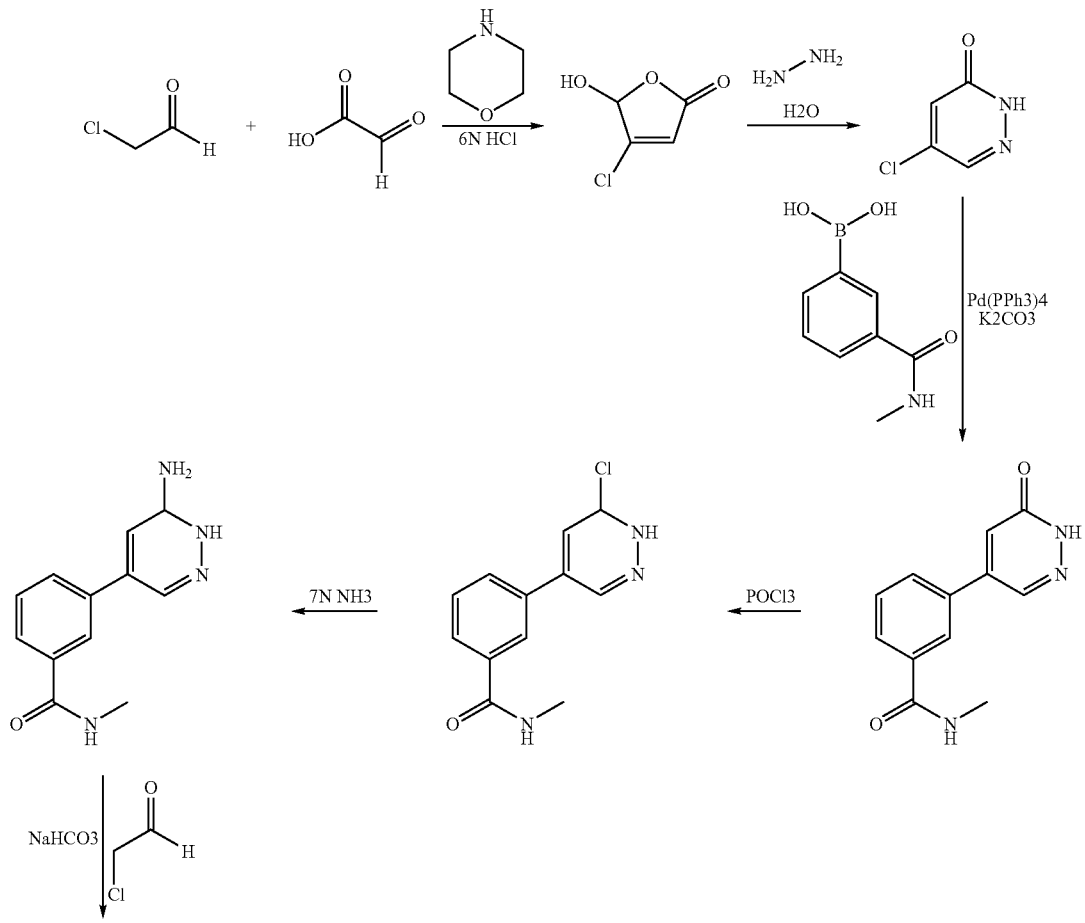

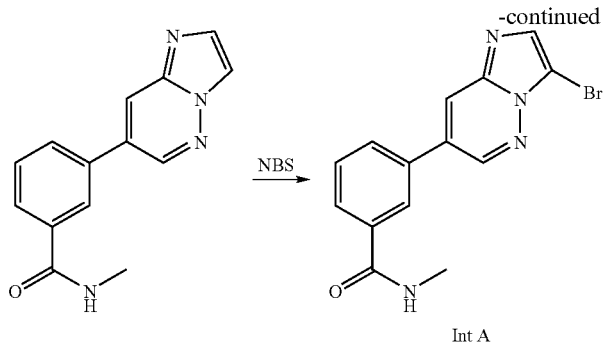

Int A

Step A: 4-Chloro-5-hydroxy-5H-furan-2-one

Morpholine (1.4 eq, 500 mmol, 44 ml) is added to HCl (6N, 120 ml) and the reaction mixture is stirred overnight at room temperature. The water is evaporated under reduced pressure to give the morpholinium chloride as a white solid. The salt is dissolved in dioxane (130 ml) and glyoxilic acid (1.5 eq, 540 mmol, 79 g) is added to the reaction mixture which is then stirred at room temperature for 1 h. After this time, chloroacetic aldehyde (1.0 eq, 360 mmol, 42.5 ml) is added and the mixture is heated at reflux for 48 hours. Dioxane is then removed in vacuo and the remaining black aqueous layer is extracted with EtOAc (4×800 ml). The dark red organic phase is dried over MgSO$_4$, filtered and evaporated to dryness to yield 4-Chloro-5-hydroxy-5H-furan-2-one as a dark red oil which did not require further purification; [M+H]$^+$=135

Step B: 5-Chloro-pyridazin-3-one

A cooled (0° C.) solution of 4-Chloro-5-hydroxy-5H-furan-2-one (1 eq, 296 mmol, 39.8 g) in acetic acid is treated slowly with hydrazine hydrate (1.3 eq, 385 mmol, 19.1 ml) and the reaction mixture is then stirred overnight at room temperature. AcOH is then removed in vacuo to give a black oil which is diluted with water (200 ml). Then the pH of the aqueous solution is adjusted to pH7 with a concentrated aqueous solution of NaOH (32%) and extracted with EtOAc. The combined organic portions (red solution) are washed with brine, dried over MgSO$_4$, filtered and evaporated to dryness. The product is purified by flash column chromatography eluting with 6:4 EtOAc/iso-hexane to afford 5-Chloro-pyridazin-3-one as a pale yellow solid; [M+H]$^+$=131

Step C: N-Methyl-3-(6-oxo-1,6-dihydro-pyridazin-4-yl)-benzamide

5-Chloro-pyridazin-3-one (1 eq, 5.06 mmol, 660 mg) and 3-(N-Methylaminocarbonyl)phenyl boronic acid (1.1 eq, 5.56 mmol, 996 mg) are dissolved in dioxane (4 ml), water (2 ml) and EtOH (2 ml) and K$_2$CO$_3$ (2 eq, 10.1 mmol, 1.40 g) is added. Pd(PPh$_3$)$_4$ (0.1 eq, 0.5 mmol, 584 mg) is then added and the reaction mixture is heated using microwave radiation at 140° C. for 20 min. The reaction mixture is diluted with EtOAc/H$_2$O and filtered. The organic layer is then separated and the aqueous layer is extracted with EtOAc (2×20 ml). The organic layer is washed with NaHCO$_3$, brine, dried over MgSO$_4$, filtered and evaporated to dryness to yield N-Methyl-3-(6-oxo-1,6-dihydro-pyridazin-4-yl)-benzamide as a white solid which did not require further purification; [M+H]$^+$=230

Step D: 3-(6-Chloro-1,6-dihydro-pyridazin-4-yl)-N-methyl-benzamide

N-Methyl-3-(6-oxo-1,6-dihydro-pyridazin-4-yl)-benzamide (1 eq, 3.14 mmol, 720 mg) is suspended in POCl$_3$ (10 ml) and the reaction mixture is heated at 110° C. for 2 h. After cooling to room temperature, the solvent is removed in vacuo and then ice water is added. The pH is adjusted to pH8 with portionwise addition of sat. aqueous Na$_2$CO$_3$. The aqueous layer is extracted with EtOAc and the combined organic layers are washed with brine, dried over MgSO$_4$, filtered and evaporated to dryness to yield 3-(6-Chloro-1,6-dihydro-pyridazin-4-yl)-N-methyl-benzamide as a yellow solid which did not require further purification; [M+H]$^+$=248

Step E: 3-(6-Amino-1,6-dihydro-pyridazin-4-yl)-N-methyl-benzamide 3-(6-Chloro-1,6-dihydro-pyridazin-4-yl)-N-methyl-benzamide (1 eq, 2.46 mmol, 610 mg) is dissolved in a solution of NH$_3$ (7N, 20 ml) in EtOH and heated at 160° C. in a sealed tube for 48 h. The solvent is then removed in vacuo. The reaction mixture is purified by flash column chromatography eluting with 8:2:0.5 DCM/MeOH/NH$_3$ to give 3-(6-Amino-1,6-dihydro-pyridazin -4-yl)-N-methyl-benzamide as a brown solid; [M+H]$^+$=229

Step F: 3-imidazo-[1,2-b]-pyridazin-7-yl-N-methyl-benzamide 3-(6-Amino-1,6-dihydro-pyridazin-4-yl)-N-methyl-benzamide (1 eq, 1.07 mmol, 245 mg) is added to a solution of chloroacetic aldehyde (5 eq, 5.4 mmol, 0.69 ml) in EtOH (15 ml). NaHCO$_3$ (2 eq, 2.15 mmol, 180 mg) is then added and the reaction mixture is heated at reflux for 17 h. The solvent is then removed in vacuo and the product is purified by flash column chromatography eluting with 9:1 DCM/MeOH to afford 3-imidazo-[1,2-b]-pyridazin-7-yl-N-methyl-benzamide as an orange solid; [M+H]$^+$=253

Step G: 3-(3-Bromo-imidazo-[1,2-b]-pyridazin-7-yl)-N-methyl-benzamide

3-Imidazo-[1,2-b]-pyridazin-7-yl-N-methyl-benzamide (1 eq, 0.595 mmol, 150 mg) is dissolved in DMF (5 ml) at 0° C. and NBS (1.1 eq, 0.654 mmol, 116 mg) is added. The reaction mixture is stirred for 1 h at 0° C. and then is diluted with EtOAc. The reaction mixture is washed with NaHCO$_3$ and brine, dried over MgSO$_4$, filtered and evaporated to yield 3-(3-Bromo-imidazo-[1,2-b]-pyridazin-7-yl)-N-methyl-benzamide as a pale yellow solid which did not require further purification; [M+H]$^+$=333

Intermediates B to L

These intermediates namely,
3-(3-Bromo-imidazo-[1,2-b]pyridazin-7-yl)phenol (Intermediate B)
3-Bromo-7-pyridin-4-yl-imidazo[1,2-b]pyridazine (Intermediate C),
N-[3-(3-Bromo-imidazo-[1,2-b]pyridazin-7-yl)-phenyl]-methanesulfonamide (Intermediate D), 3-Bromo-7-pyridin-3-yl-imidazo[1,2-b]pyridazine (Intermediate E),
N-[3-(3-Bromo-imidazo-[1,2-b]pyridazin-7-yl)-phenyl]-acetamide (Intermediate F), 3-Bromo-7-(3-fluoro-phenyl)-imidazo-[1,2-b]pyridazine (Intermediate G),
4-(3-Bromo-imidazo-[1,2-b]pyridazin-7-yl)benzoic acid ethyl ester (Intermediate H),
7-(3-Benzyloxy-phenyl)-3-bromo-imidazo-[1,2-b]pyridazine (Intermediate I),
3-Bromo-7-(3-methoxy-phenyl)-imidazo-[1,2-b]pyridazine (Intermediate J), 3-(3-Bromo-imidazo-[1,2-b]pyridazin-7-yl)-benzoic acid ethyl ester (Intermediate K),
[5-(3-Bromo-imidazo-[1,2-b]pyridazin-7-yl)-pyridin-2-yl]-dimethyl-amine (Intermediate L),
3-Bromo-7-[6-(4-methyl-piperazin-1-yl)-pyridin-3-yl]-imidazo[1,2-b]pyridazine (Intermediate M),
3-Bromo-7-(6-morpholin-4-yl-pyridin-3-yl)-imidazo[1,2-b]pyridazine (Intermediate N),
are prepared by an analogous method to 3-(3-Bromo-imidazo-[1,2-b]-pyridazin-7-yl)-N-methyl-benzamide (Intermediate A) by replacing 3-(N-Methylaminocarbonyl)phenyl boronic acid (Step C) with the corresponding boronic acid or boronic ester, namely,
3-Hydroxyphenyl boronic acid (Sigma Aldrich),
4-Pyridine boronic acid (Sigma Aldrich),
3-Methylsulfonylaminophenyl boronic acid (Combi Block),
3-Pyridine boronic acid (Sigma Aldrich),
3-Acetamidophenylboronic acid (Sigma Aldrich),
3-Fluorophenyl boronic acid (Sigma Aldrich),
4-Ethoxycarbonylphenyl boronic acid (Sigma Aldrich),
3-Benzyloxyphenyl boronic acid (Sigma Aldrich),
3-Methoxyphenyl boronic acid (Sigma Aldrich),
3-Ethoxycarbonylphenyl boronic acid (Sigma Aldrich),
(2-Dimethylamino) pyridine-5-boronic acid hydrate (Frontier Scientific),
1-Methyl-4-[5-(4,4,5,5-tetramethyl-1,3,2-dioxaborolan-2-yl)pyridin-2-yl]piperazine (ABCR GmbH & Co. KG),
6-(Morpholin-4-yl)pyridine-3-boronic acid pinacol ester (Sigma Aldrich), respectively, In the examples above, the company names given as sources have the following meanings:
Sigma Aldrich: Sigma Aldrich Corporation, St. Louis, USA;
Combi Block Combi-Blocks Inc., San Diego, Calif., USA;
Chembridge: Chembridge Corp., San Diego, Calif., USA;
Frontier Scientific Frontier Scientific, Inc., Logan, Utah, USA;
ABCR GmbH & Co. KG: ABCR GmbH & Co. KG, Karlsruhe, Germany.

Example 61

Pharmaceutical Formulation

Tablets, comprising as active ingredient 100 mg of one of the active compounds of the preceding examples, respectively, are prepared with the following composition, following standard procedures:

| Composition | |
|---|---|
| Active ingredient | 100 mg |
| Crystalline lactose | 240 mg |
| Avicel | 80 mg |
| PVPPXL | 20 mg |
| Aerosil | 2 mg |
| Magnesium stearate | 5 mg |
| | 447 mg |

Manufacture: The active ingredient is admixed with the carrier materials and compressed by means of a tabletting machine (Korsch EKO, Stempeldurchmesser 10 mm).
Avicel® is microcrystalline cellulose (FMC, Philadelphia, USA).
PVPPXL is polyvinyl polypyrrolidone, cross-linked (BASF, Ludwigshafen, Germany).
Aerosil® is silicium dioxie (Degussa, Germany).

The invention claimed is:
1. A compound of formula I

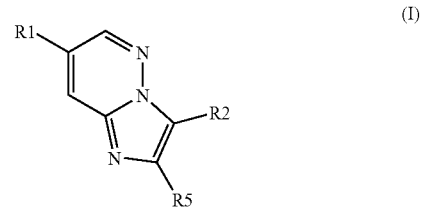

in free or salt form, wherein
R1 is aryl or heterocyclyl,
R1 being optionally substituted by one or more groups R3 independently selected from: hydroxyl, carbonyl, aminocarbonyl, $C_1$-$C_7$ alkylaminocarbonyl, amino, $C_1$-$C_7$ alkylamino, $C_1$-$C_7$ alkylthio, sulfonylamino, carbonylamino, $C_1$-$C_7$ alkylcarbonylamino, halo, carboxy, $C_1$-$C_7$ alkoxy, benzyloxy, $C_1$-$C_7$ alkyloxycarbonyl, aminosulfonyl, $C_1$-$C_7$ alkyl, cyano, sulfonyl, sulfanyl, sulfoxide, aryl, heterocyclyl, carbonyloxy, amino $C_1$-$C_7$ alkyl, $C_1$-$C_7$ alkylamino-$C_1$-$C_7$ alkyl, aryl-$C_1$-$C_7$-alkyl and heterocyclyl-$C_1$-$C_7$-alkyl, $C_4$-$C_{15}$-cycloalkenyl and $C_2$-$C_8$-cycloalkynyl; and when R3 includes two groups, such R3 groups may be joined together to form a ring which is fused to R1;
wherein R3 is optionally substituted by one or more groups selected from hydroxyl, $C_1$-$C_7$ alkyl, aryl, amino, $C_1$-$C_7$ alkylamino, heterocyclyl, cyano, halo, sulfonyl, sulfanyl, sulfoxide, di($C_1$-$C_7$) alkylamino, hydroxyl-$C_1$-$C_7$ alkyl, alkoxy, di-$C_1$-$C_7$ alkylamino-$C_1$-$C_7$ alkyl;
R2 is aryl, heteroaryl, heteroaryl-aryl, heteroaryl-heterocyclyl, aryl-heterocyclyl, biaryl, heterocyclyl-heterocyclyl;
R2 being optionally substituted by one or more groups R4 independently selected from aryl, heteroaryl, heterocloalkyl, $C_1$-$C_7$ alkyl, $C_3$-$C_{10}$-cycloalkyl, aminocarbonyl, $C_1$-$C_7$ alkylaminocarbonyl, halo, $C_1$-$C_7$ alkoxy, $C_1$-$C_7$ alkylthio, hydroxyl, $C_1$-$C_7$ alkylcarbonyl, carboxy, carbonyl, cyano, sulfonamide and from $C_4$-$C_{15}$-cycloalkenyl; and when R4 includes two groups, such R4 groups may be joined together to form a ring which is fused to R2;
wherein R4 is optionally substituted by one or more groups selected from hydroxyl, $C_1$-$C_7$ alkyl, aryl, amino, $C_1$-$C_7$ alkylamino, heterocyclyl, cyano, halo, sulfonyl, sulfanyl, sulfoxide;
R5 is H or $NH_2$.
2. A compound in free or salt form according to claim 1 wherein
R1 is aryl or heterocyclyl
R1 being optionally substituted by one or more groups R3 independently selected from: hydroxyl, carbonyl, aminocarbonyl, $C_1$-$C_7$ alkylaminocarbonyl, amino, $C_1$-$C_7$ alkylamino, $C_1$-$C_7$ alkylthio, sulfonylamino, carbonylamino, $C_1$-$C_7$ alkylcarbonylamino, halo, carboxy, C₁-C₇ alkoxy, benzyloxy, C₁-C₇ alkyloxycarbonyl, aminosulfonyl, C₁-C₇ alkyl, cyano, sulfonyl, sulfanyl, sulfoxide, aryl, heterocyclyl, carbonyloxy, amino C₁-C₇ alkyl and C₁-C₇ alkylamino-C₁-C₇ alkyl; and when R3 includes two groups, such R3 groups may be joined together to form a ring which is fused to R1;

wherein R3 is optionally substituted by one or more groups selected from hydroxyl, C₁-C₇ alkyl, aryl, amino, C₁-C₇ alkylamino, heterocyclyl, cyano, halo, sulfonyl, sulfanyl, sulfoxide, di(C₁-C₇) alkylamino, hydroxyl-C₁-C₇ alkyl, alkoxy, di-C₁-C₇ alkylamino-C₁-C₇ alkyl;

and R2 is defined as in claim 1.

3. A compound according to claim 1 wherein R1 is optionally substituted phenyl or pyridinyl.

4. A compound according to claim 1 wherein R2 is optionally substituted phenyl or pyridinyl.

5. A compound in free or salt form, selected from the group consisting of
- N-methyl-3-[3-(2-phenyl-pyridin-4-yl)-imidazo[1,2-b]pyridazin-7-yl]-benzamide,
- 3-[3-(2-furan-3-yl-pyridin-4-yl)-imidazo[1,2-b]pyridazin-7-yl]-N-methyl-benzamide,
- 3-{3-[2-(3-fluoro-phenyl)-pyridin-4-yl]-imidazo[1,2-b]pyridazin-7-yl}-N-methyl-benzamide,
- 3-[3-(2-furan-2-yl-pyridin-4-yl)-imidazo[1,2-b]pyridazin-7-yl]-N-methyl-benzamide,
- 3-{3-[2-(4-fluoro-phenyl)-pyridin-4-yl]-imidazo[1,2-b]pyridazin-7-yl}-N-methyl-benzamide,
- 3-(2-phenyl-pyridin-4-yl)-7-pyridin-4-yl-imidazo[1,2-b]pyridazine,
- 3-(2-furan-3-yl-pyridin-4-yl)-7-pyridin-4-yl-imidazo[1,2-b]pyridazine,
- N-{3-[3-(2-furan-3-yl-pyridin-4-yl)-imidazo[1,2-b]pyridazin-7-yl]-phenyl}-methanesulfonamide,
- 3-{-4-[7-(3-methanesulfonylamino-phenyl)-imidazo[1,2-b]pyridazin-3-yl]-pyridin-2-yl}-benzamide,
- 7-(3-fluoro-phenyl)-3-(2-thiophen-3-yl-pyridin-4-yl)-imidazo[1,2-b]pyridazine,
- 7-(3-fluoro-phenyl)-3-(2-furan-3-yl-pyridin-4-yl)-imidazo[1,2-b]pyridazine,
- 7-(3-fluoro-phenyl)-3-(2-phenyl-pyridin-4-yl)-imidazo[1,2-b]pyridazine,
- 3-{4-[7-(3-fluoro-phenyl)-imidazo[1,2-b]pyridazin-3-yl]-pyridin-2-yl}-benzamide,
- 7-[6-(4-methyl-piperazin-1-yl)-pyridin-3-yl]-3-(2-phenyl-pyridin-4-yl)-imidazo[1,2-b]pyridazine,
- 7-(3-benzyloxy-phenyl)-3-(2-furan-3-yl-pyridin-4-yl)-imidazo[1,2-b]pyridazine,
- 3-(2-furan-3-yl-pyridin-4-yl)-7-(3-methoxy-phenyl)-imidazo[1,2-b]pyridazine,
- 7-(3-methoxy-phenyl)-3-(2-phenyl-pyridin-4-yl)-imidazo[1,2-b]pyridazine,
- 4-[7-(3-methoxy-phenyl)-imidazo[1,2-b]pyridazin-3-yl]-[2,4']bipyridinyl,
- 3-[3-(2-furan-3-yl-pyridin-4-yl)-imidazo[1,2-b]pyridazin-7-yl]-benzoic acid ethyl ester,
- 3-[3-(2-phenyl-pyridin-4-yl)-imidazo[1,2-b]pyridazin-7-yl]-benzoic acid ethyl ester,
- dimethyl-{5-[3-(2-thiophen-3-yl-pyridin-4-yl)-imidazo[1,2-b]pyridazin-7-yl]-pyridin-2-yl}-amine,
- dimethyl-(5-{3-[2-(5-methyl-furan-2-yl)-pyridin-4-yl]-imidazo[1,2-b]pyridazin-7-yl}-pyridin-2-yl)-amine,
- {5-[3-(2-furan-3-yl-pyridin-4-yl)-imidazo[1,2-b]pyridazin-7-yl]-pyridin-2-yl}-amine,
- dimethyl-{5-[3-(2-phenyl-pyridin-4-yl)-imidazo[1,2-b]pyridazin-7-yl]-pyridin-2-yl}-amine,
- 4-[3-(2-phenyl-pyridin-4-yl)-imidazo[1,2-b]pyridazin-7-yl]-benzoic acid ethyl ester,
- N-methyl-3-[3-(3-pyrazol-1-yl-phenyl)-imidazo[1,2-b]pyridazin-7-yl]-benzamide,
- 4-[7-(3-methylcarbamoyl-phenyl)-imidazo[1,2-b]pyridazin-3-yl]-pyridine-2-carboxylic acid methylamide,
- 3-[3-(3-pyrazol-1-yl-phenyl)-imidazo[1,2-b]pyridazin-7-yl]-phenol,
- 4-[7-(3-hydroxy-phenyl)-imidazo[1,2-b]pyridazin-3-yl]-2-methoxy-phenol,
- 3-(2-chloro-pyridin-4-yl)-7-pyridin-4-yl-imidazo[1,2-b]pyridazine,
- 2-methoxy-4-(7-pyridin-4-yl-imidazo[1,2-b]pyridazin-3-yl)-phenol,
- N-{3-[3-(2-chloro-pyridin-4-yl)-imidazo[1,2-b]pyridazin-7-yl]-phenyl}-methanesulfonamide,
- 4-[7-(3-methanesulfonylamino-phenyl)-imidazo[1,2-b]pyridazin-3-yl]-benzamide,
- 3-(3-pyrazol-1-yl-phenyl)-7-pyridin-3-yl-imidazo[1,2-b]pyridazine,
- 3-(7-pyridine-3-yl-imidazo[1,2-b]pyridazin-3-yl)-benzamide,
- 2-methoxy-4-(7-pyridin-3-yl-imidazo[1,2-b]pyridazin-3-yl)-phenol,
- 3-(7-pyridine-3-yl-imidazo[1,2-b]pyridazin-3-yl)-benzoic acid,
- 1-[3-(7-pyridin-3-yl-imidazo[1,2-b]pyridazin-3-yl)-phenyl]-ethanone,
- N-{3-[3-(3-pyrazol-1-yl-phenyl)-imidazo[1,2-b]pyridazin-7-yl]-phenyl}-acetamide,
- 3-[7-(3-fluoro-phenyl)-imidazo[1,2-b]pyridazin-3-yl]benzamide,
- 7-(3-fluoro-phenyl)-3-(3-pyrazol-1-yl-phenyl)-imidazo[1,2-b]pyridazine,
- 4-[7-(3-fluoro-phenyl)-imidazo[1,2-b]pyridazin-3-yl]-2-methoxy-phenol,
- 7-[6-(4-methyl-piperazin-1-yl)-pyridin-3-yl]-3-[2-(1H-pyrazol-4-yl)-pyridin-4-yl]-imidazo [1,2-b]pyridazine,
- 7-(6-morpholin-4-yl-pyridin-3-yl)-3-(3-pyrazol-1-yl-phenyl)-imidazo[1,2-b]pyridazine,
- 4-[3-(3-pyrazol-1-yl-phenyl)-imidazo[1,2-b]pyridazin-7-yl]-benzoic acid ethyl ester,
- 2-methoxy-4-[7-(3-methoxy-phenyl)-imidazo[1,2-b]pyridazin-3-yl]-phenol,
- 3-[3-(4-hydroxy-3-methoxy-phenyl)-imidazo[1,2-b]pyridazin-7-yl]-benzoic acid ethyl ester,
- dimethyl-{5-[3-(3-pyrazol-1-yl-phenyl)-imidazo[1,2-b]pyridazin-7-yl]-pyridin-2-yl}-amine,
- N-(2-hydroxy-ethyl)-4-[3-(3-pyrazol-1-yl-phenyl)-imidazo-[1,2-b]-pyridazin-7-yl]-benzamide,
- N-(2-hydroxy-ethyl)-4-[3-(2-phenyl-pyridin-4-yl)-imidazo-[1,2-b]-pyridazin-7-yl]-benzamide,
- {3-[3-(2-furan-3-yl-pyridin-4-yl)-imidazo[1,2-b]pyridazin-7-yl]-phenyl}-methanol,
- -[3-(2-phenyl-pyridin-4-yl)-imidazo[1,2-b]pyridazin-7-yl]-benzoic acid
- 3-[3-(4-hydroxy-3-methoxy-phenyl)-imidazo-[1,2-b]-pyridazin-7-yl]-benzoic acid,
- 3-(2-amino-3-(2-phenyl-pyridin-4-yl)-imidazo[1,2-b]pyridazin-7-yl)-N-methyl-benzamide
- N-(3-dimethylamino-propyl)-3-[3-(2-phenyl-pyridin-4-yl)-imidazo[1,2-b]pyridazin-7-yl]-benzamide,
- 3-[3-(2-phenyl-pyridin-4-yl)-imidazo[1,2-b]pyridazin-7-yl]-N-(2-piperidin-1-yl-ethyl)-benzamide,
- N-methyl-N-(2-methylamino-ethyl)-3-[3-(2-Phenyl-pyridin-4-yl)-imidazo[1,2-b]pyridazin-7-yl]-benzamide, N-(2-hydroxy-ethyl)-3-[3-(2-Phenyl-pyridin-4-yl)-imidazo[1,2-b]pyridazin-7-yl]-benzamide,
N-butyl-3-[3-(2-Phenyl-pyridin-4-yl)-imidazo[1,2-b]pyridazin-7-yl]-benzamide and
1-(3-piperidin-1-yl-propyl)-4-[3-(3-pyrazol-1-yl-phenyl)-imidazo[1,2-b]pyridazin-7-yl]-1H-pyridin-2-one.

6. A pharmaceutical composition comprising a compound according to claim 1, in admixture with a pharmaceutically acceptable excipient, diluent or carrier.

7. A method of treating bone conditions which are associated with increased calcium depletion or resorption or in which stimulation of bone formation and calcium fixation in the bone is desirable comprising administering a compound according to claim 1 in an effective amount to a patient in need thereof.

* * * * *